(12) United States Patent
Vilaplana et al.

(10) Patent No.: US 11,130,825 B2
(45) Date of Patent: Sep. 28, 2021

(54) ENZYMATIC-ASSISTED HYDROTHERMAL EXTRACTION OF HEMICELLULOSES

(71) Applicant: LANTMÄNNEN EK FÖR, Stockholm (SE)

(72) Inventors: Francisco Vilaplana, Stockholm (SE); Andrea Caroline Ruthes, Stockholm (SE)

(73) Assignee: LANTMÄNNEN EK FÖR, Stockholm (SE)

( * ) Notice: Subject to any disclaimer, the term of this patent is extended or adjusted under 35 U.S.C. 154(b) by 386 days.

(21) Appl. No.: 15/735,694

(22) PCT Filed: Jun. 10, 2016

(86) PCT No.: PCT/EP2016/063372
§ 371 (c)(1),
(2) Date: Dec. 12, 2017

(87) PCT Pub. No.: WO2016/198651
PCT Pub. Date: Dec. 15, 2016

(65) Prior Publication Data
US 2020/0040110 A1 Feb. 6, 2020

(30) Foreign Application Priority Data
Jun. 17, 2015 (SE) .................................. 1550840-1

(51) Int. Cl.
*C08B 37/00* (2006.01)
*A23L 33/24* (2016.01)
(Continued)

(52) U.S. Cl.
CPC .......... *C08B 37/0057* (2013.01); *A23L 7/107* (2016.08); *A23L 33/24* (2016.08); *A61K 31/715* (2013.01); *A23V 2002/00* (2013.01)

(58) Field of Classification Search
CPC .............................. B08B 37/0057; A23L 33/24
(Continued)

(56) References Cited

U.S. PATENT DOCUMENTS

| 2005/0089602 A1 | 4/2005 | Kvist et al. |
| 2012/0009626 A1 | 1/2012 | Suzuki et al. |
| 2012/0009642 A1 | 1/2012 | Suzuki et al. |

FOREIGN PATENT DOCUMENTS

| GB | 2506125 A | 3/2014 |
| JP | 5-219976 A | 8/1993 |

(Continued)

OTHER PUBLICATIONS

Carvajal-Millan et al., Arabinoxylan Gels: Impact of the Feruloylation Degree on Their Structure and Properties, 2005, Biomacromolecules, 6, 1, pp. 309-317 (Year: 2005).*

(Continued)

*Primary Examiner* — Holly Kipouros
(74) *Attorney, Agent, or Firm* — Cermak Nakajima & McGowan LLP; Malcolm K. McGowan

(57) ABSTRACT

The present invention relates to a novel process for producing hemicellulose fractions from cereal crops, comprising pressurized hot water extraction of hemicellulose fractions from cereal crops in combination with subsequent enzymatic treatments and/or subsequent membrane ultrafiltration to further purify the extracts. The novel process described herein allows for sustainable and scalable extraction and isolation of valuable hemicellulose fractions, especially arabinoxylans (AXs), from cereal side products. The process allows the selective fractionation of arabinoxylans based on their molecular structure and inherent functionalities, which can e.g. be used for the preparation of carbohydrate-based materials with functional properties.

14 Claims, 16 Drawing Sheets

Figure 1:
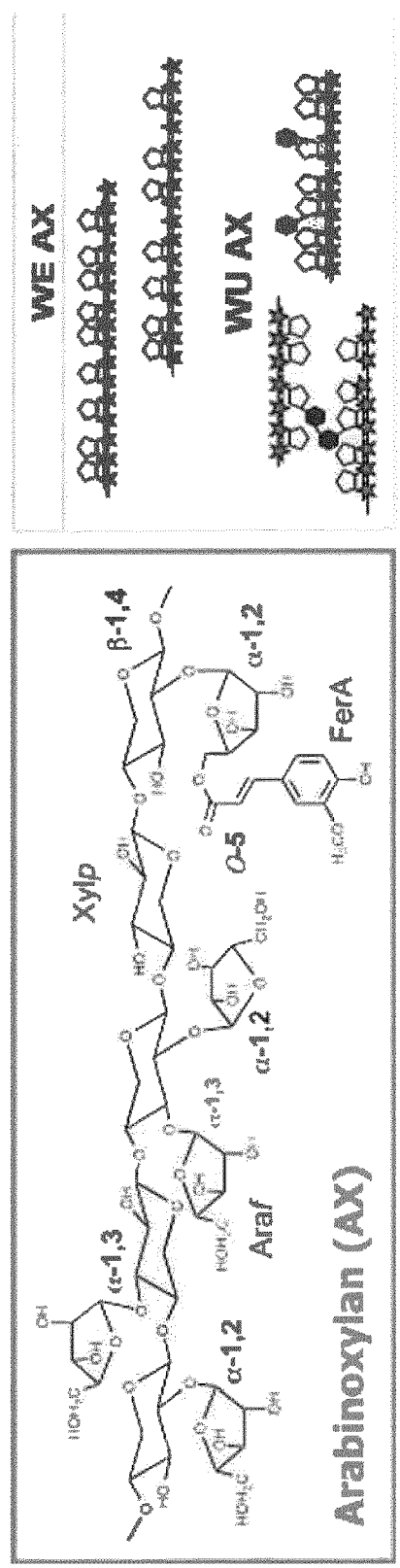

(51) Int. Cl.
*A23L 7/104* (2016.01)
*A61K 31/715* (2006.01)

(58) Field of Classification Search
USPC .......................................................... 435/277
See application file for complete search history.

(56) References Cited

FOREIGN PATENT DOCUMENTS

| JP | 3079115 B2 | 6/2000 |
| SE | 541673 C2 | 11/2019 |
| WO | WO99/11672 A1 | 3/1999 |
| WO | WO01/67891 A1 | 9/2001 |
| WO | WO2008/000050 A2 | 1/2008 |
| WO | WO2008/000050 A3 | 1/2008 |
| WO | WO2008/017145 A1 | 2/2008 |
| WO | WO2014/019589 A1 | 2/2014 |
| WO | WO2014/158774 A1 | 10/2014 |
| WO | WO2015/014361 A2 | 2/2015 |
| WO | WO2015/014364 A1 | 2/2015 |

OTHER PUBLICATIONS

Faulds et al., Specificity of feruloyl esterases for water-extractable and water-unextractable feruloylated polysaccharides: influence of xylanase, 2003, Journal of Cereal Science, 38, pp. 281-288 (Year: 2003).*

Coelho et al., Microwave superheated water and dilute alkali extraction of brewers' spent grain arabinoxylans and arabinoxylo-oligosaccharides, 2014, Carbohydrate Polymers, 99, pp. 415-422 (Year: 2014).*

Nin~o-Medina et al., Feruloylated arabinoxylans and arabinoxylan gels: structure, sources and applications, 2009, Phytochem Review, 9:111-120 (Year: 2009).*

Vardakou et al., Evaluation of the prebiotic properties of wheat arabinoxylan fractions and induction of hydrolase activity in gut microflora, International Journal of Food Microbiology, 2008, 123: 166-170 (Year: 2008).*

Frederix et al., Water-Extractable and Water-Unextractable Arabinoxylans Affect Gluten Agglomeration Behavior during Wheat Flour Gluten-Starch Separation, 2004, Journal of Agricultural and Food Chemistry, 52, pp. 7950-7956 (Year: 2004).*

Aguedo, M., et al., "Extraction by three processes of arabinoxylans from wheat bran and characterization of the fractions obtained," Carbohydrate Polymers 2014;105:317-324.

Holopainen-Mantila, U., et al., "Impact of hydrothermal pretreatment to chemical composition, enzymatic digestibility and spatial distribution of cell wall polymers," Bioresource Technology 2013;138:156-162.

Izydorczyk, M. S., et al., "Cereal arabinoxylans: advances in structure and physicochemical properties," Carbohydrate Polymers 1995;28:33-48.

Izydorczyk, M. S., et al., "Barley B-glucans and arabinoxylans: Molecular structure, physicochemical properties, and uses in good products-a Review," Food Research International 2008;41:850-868.

Merali, Z., et al., "Characterization of cell wall components of wheat bran following hydrothermal pretreatment and fractionation," Biotechnology for Biofuels 2015;8(23):pp. 1-13.

Reisinger, M., et al., "Wheat bran biorefinery—A detailed investigation on hydrothermal and enzymatic treatment," Bioresource Technology 2013;144:179-185.

Sarkar, S., et al., "Relevance of ions in pressurized fluid extraction of carbohydrates and phenolics from barley hull," Journal of Supercritical Fluids 2014;93:27-37.

Saulnier, L., et al., "Wheat arabinoxylans: Exploiting variation in amount and composition to develop enhanced varieties," Journal of Cereal Science 2007;46:261-281.

Steiner, J., et al., "Brewer's spent grain: source of value-added polysaccharides for the food industry in reference to the health claims," Eur. Food Res. Technol. 2015;241:303-315.

International Search Report for PCT Patent App. No. PCT/EP2016/063372 (dated Nov. 25, 2017).

Written Opinion for PCT Patent App. No. PCT/EP2016/063372 (dated Nov. 25, 2017).

Merali, Z., et al., "Characterization of cell wall components of wheat bran following hydrothermal pretreatment and fractionation," Biotechnol. for Biofuels 2015, vol. 8, No. 23, pp. 1-13.

* cited by examiner

Fig.1A/B

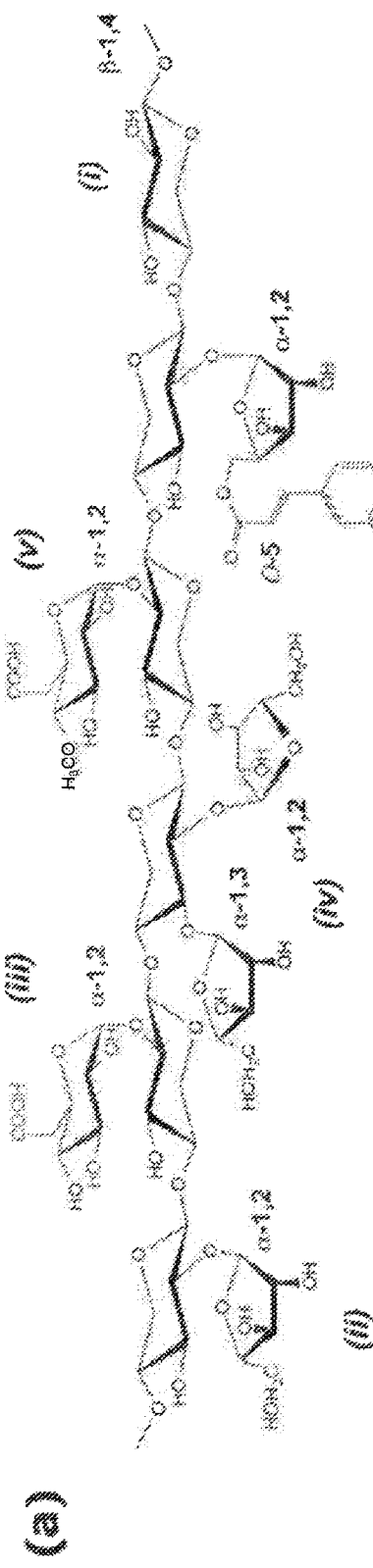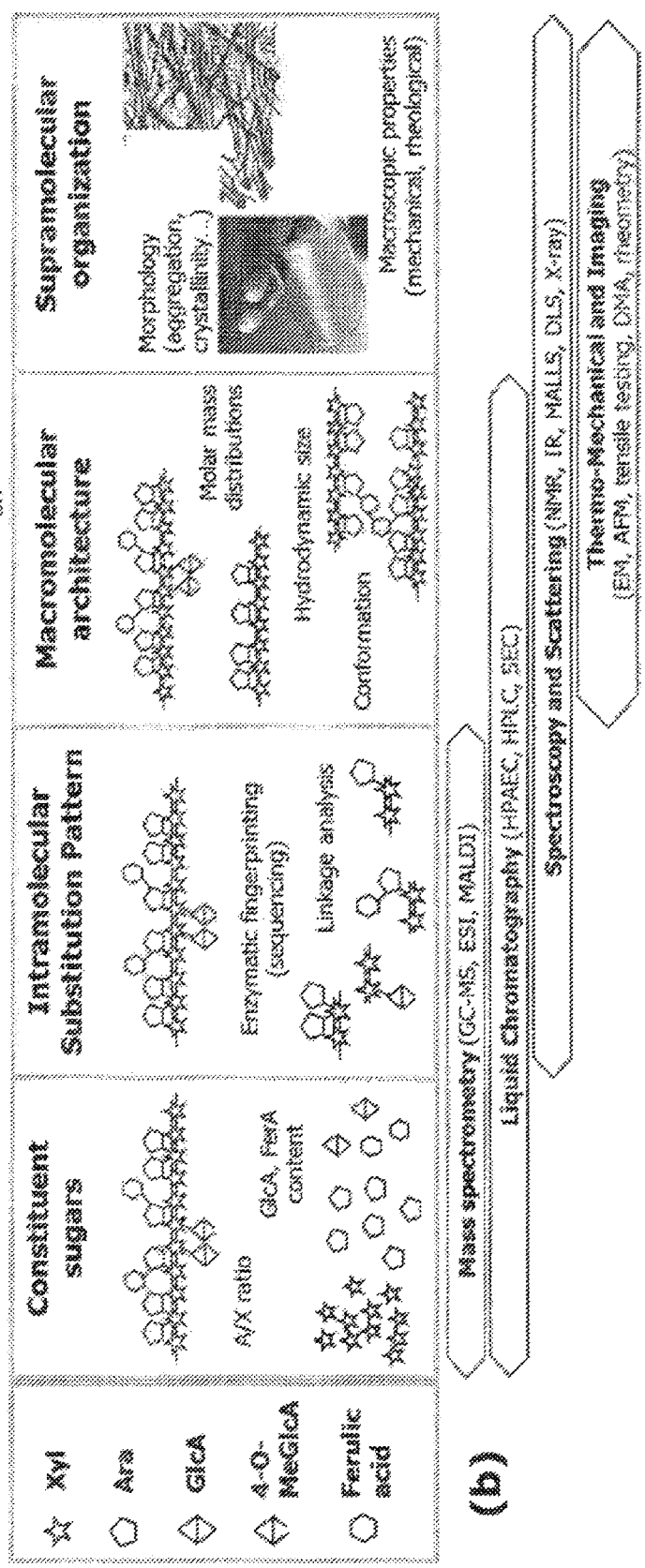
Fig. 6

Figure 8A:
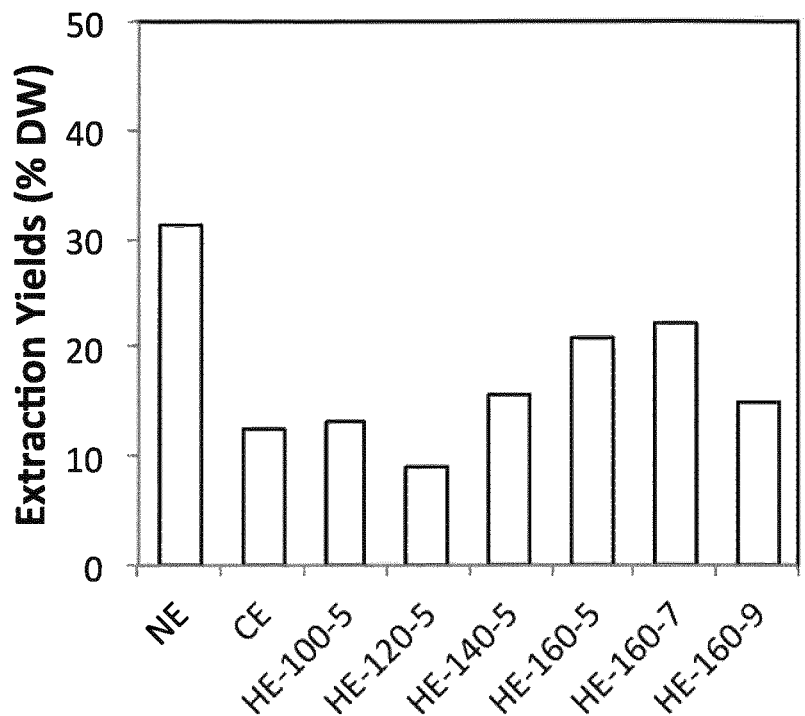

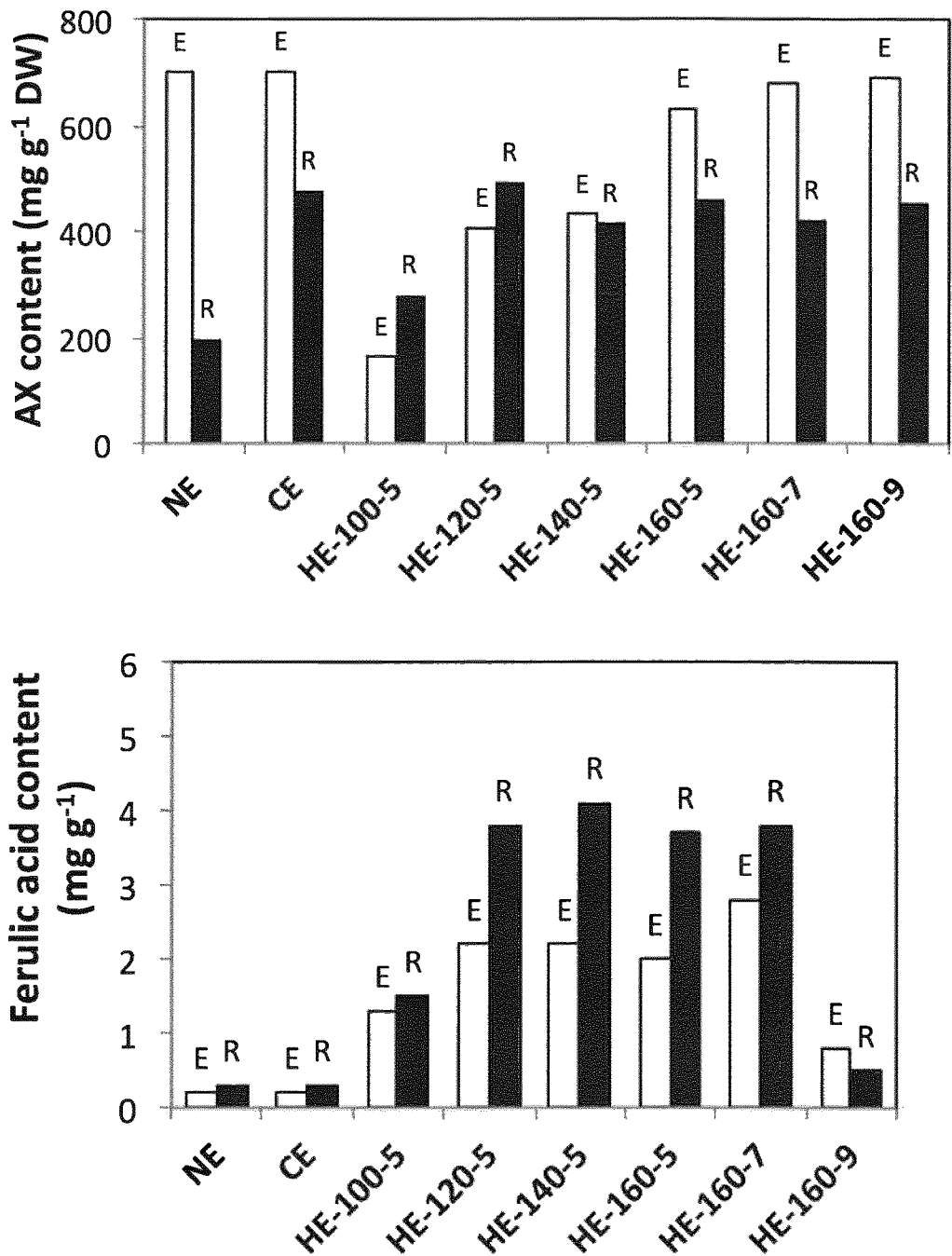
Fig.8B/C

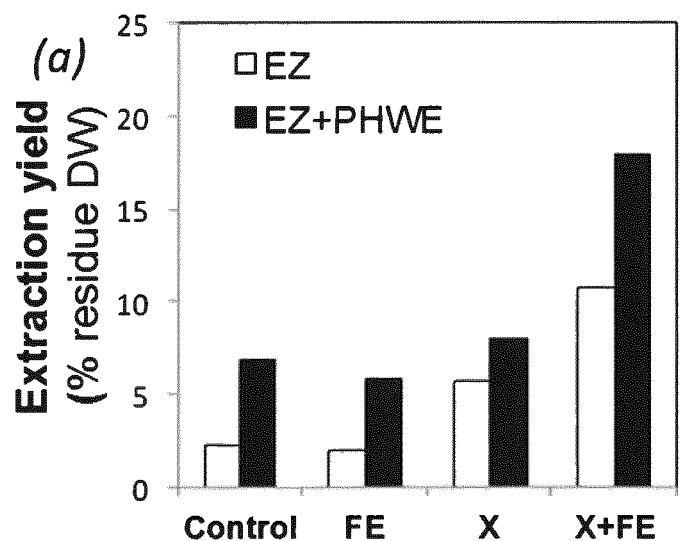
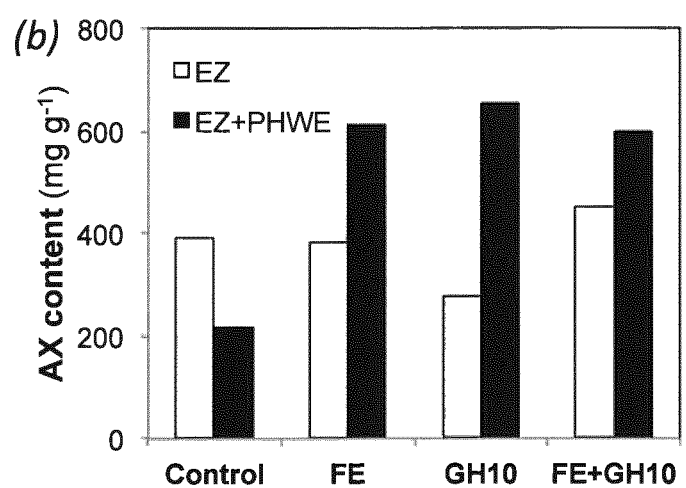
Fig.11

ENZYMATIC-ASSISTED HYDROTHERMAL EXTRACTION OF HEMICELLULOSES

CROSS-REFERENCE TO RELATED APPLICATIONS

This application is a National Stage Entry of PCT/EP2016/063372, filed Jun. 10, 2016, which claims priority from Swedish patent application 1550840-1, filed Jun. 17, 2015. The contents of these priority applications are incorporated herein by reference in their entirety.

FIELD OF INVENTION

The present invention relates to a novel process for producing hemicellulose fractions from cereal crops, comprising pressurized hot water extraction (PHWE) of hemicellulose fractions from cereal crops in combination with enzymatic treatments of the residue after extraction and/or membrane ultrafiltration of the extract. The novel process described herein allows for sustainable and scalable extraction and isolation of valuable hemicellulose fractions, especially arabinoxylans (AXs) in polymeric as well as in polymeric and oligomeric form, from cereal side products. The process allows the selective fractionation of arabinoxylans based on their molecular structure and inherent functionalities, which can e.g. be used for the preparation of carbohydrate-based materials with functional properties and/or food products. Optionally, the process can include a pretreatment of the cereal crops before the pressurized hot water extraction.

The obtained polymeric and oligomeric hemicellulose fractions show significant antioxidant properties compared with equivalent fractions obtained by traditional alkaline processes.

BACKGROUND OF THE INVENTION

Hemicelluloses constitute a rich cell wall polysaccharide fraction in cereal crops, both in the grain (as non-starch polysaccharides) and in the straw (associated with cellulose fibres and lignins). These polysaccharide fractions represent a valuable renewable resource that has not been hitherto exploited to the full potential for high-value applications. The valorization of such agricultural by-products is therefore fundamental for a complete implementation of first and second generation biorefineries handling cereal grain and lignucellulosic straw waste streams, respectively[1].

Arabinoxylan (AX) is the most abundant hemicellulose in cereals as part of the grain (as non-starch polysaccharides) and the straw (associated with cellulose fibres and lignins), with an average composition of 30% in such tissues[2,3]. Cereal AXs consist of a backbone of 1,4-β-D-xylopyranose (Xylp) units, which are heavily substituted by arabinofuranosyl units (Araf) in the α-1,2 and/or α-1,3 positions to different extents and intramolecular distributions, depending on the biological source and tissue.[4] The arabinose decorations may be further substituted by ester links in the C5 position by phenolic compounds, mainly ferulic acid (FerA); these phenolic compounds can dimerise with other aromatic moieties, creating a complex crosslinked covalent structure[5] (FIG. 1a).

From a technological point of view, cereal AXs have been traditionally classified in water-extractable (WE-AX) and water-unextractable arabinoxylans (WU-AX), depending on their potential aqueous extractability at room temperature[3] (FIG. 1b). WE-AXs are mainly present in the cereal endosperm and are moderately substituted with arabinose. On the contrary, WU-AXs are predominant in cereal bran, representing approximately 95% of the total estimated AX content[3,4,6-8]. WU-AXs show great heterogeneity in their structure[9], with fractions containing very divergent Araf substitution patterns and further substituted with ferulic acid, which contribute to crosslinking with other arabinoxylan polymers and other cell wall components. This molecular heterogeneity has a great impact on the extractability of these hemicelluloses and on their macroscopic properties (e.g. solubility, rheological, film forming and mechanical properties), which are fundamental for their material applications.

SUMMARY OF THE PRESENT INVENTION

Hemicelluloses in cereal byproducts represent a valuable renewable resource that has not been exploited to full capacity yet.

The present invention for the first time describes a sustainable and scalable approach to extract and isolate valuable hemicellulose fractions in the aqueous phase, especially arabinoxylans (AXs) and feruloylated arabinoxylans (F-AX), from cereal side products comprising exposing cereal crops to one or more pressurized hot water extraction(s) (PHWE) in combination with one or more subsequent enzymatic treatment(s) of the extraction residue. One or more optional enzymatic pretreatment(s) may be added prior to the pressurized hot water extraction(s), e.g. if the cereal byproduct contains large amounts of starch (non-destarched cereal side products) and/or fat. This process allows for selective fractionation of arabinoxylans based on their molecular structure and inherent functionalities, which can be used for the preparation of carbohydrate-based materials with functional properties and/or food products.

In another embodiment, the present invention for the first time describes a sustainable and scalable approach to extract and isolate valuable hemicellulose fractions in the aqueous phase, especially arabinoxylans (AXs), from cereal side products comprising exposing cereal crops to one or more pressurized hot water extraction(s) (PHWE) in combination with one or more steps of subsequent membrane ultrafiltration to further purify the extracts and to fractionate them into a polymeric and oligomeric fraction. One or more optional enzymatic pretreatment(s) may be added prior to the pressurized hot water extraction(s), e.g. if the cereal byproduct contains large amounts of starch (non-destarched cereal side products) and/or fat. This process allows for selective fractionation of arabinoxylans based on their molecular structure and inherent functionalities, which can be used for the preparation of carbohydrate-based materials with functional properties and/or food products.

In a presently preferred embodiment, the invention relates to a sustainable and scalable approach to extract and isolate valuable hemicellulose fractions in the aqueous phase, especially arabinoxylans (AXs), from cereal side products comprising exposing cereal crops to one or more pressurized hot water extraction(s) (PHWE) in combination with one or more subsequent enzymatic treatment(s) of the extraction residue in combination with one or more steps of subsequent membrane ultrafiltration to further purify the extracts. Again, one or more optional enzymatic pretreatment(s) may be added prior to the pressurized hot water extraction(s), if the cereal byproduct e.g. contains large amounts of starch (non-destarched cereal side products) and/or fat.

The present invention relates to a process for producing a hemicellulose fraction from a cereal crop, such as from a cereal byproduct, comprising subjecting said cereal crop to pressurized hot water extraction and enzymatic treatment(s). The (hydrothermal) pressurized hot water extraction can be performed in two steps, wherein step a) comprises a pressurized hot water extraction and step b) comprises a subsequent enzymatic treatment of the residual (non-extracted) fraction. The (hydrothermal) pressurized hot water extraction process is typically performed at a temperature at between 140-160° C. at a pH between pH5-7 on an industrial scale.

In one embodiment, the (hydrothermal) pressurized hot water extraction in step a) is performed at 160° C. in pH7.

The enzymatic treatment can comprise enzymes with polysaccharide activity. Typically, different polysaccharide fractions are isolated from each other during the herein described process, leading in one embodiment to the isolation of high molar mass arabinoxylans (AXs) and low molar mass arabinoxylan oligosaccharides (AXOs).

Typically, enzymes used in the enzymatic treatment step of the residual (non-extracted) fraction are selected from the group comprising glucanases, e.g. lichenases, cellulases, xylanases and hydrolases, e.g. esterases. In particular, endo β-xylanase and/or feruloyl esterase are enzymes that can be used for the enzymatic treatment of the residual (non-extracted) fraction.

In one embodiment, the process includes a fractionation procedure by membrane ultrafiltration to separate the high molar mass arabinoxylans above 30 000 g mol-1, such as between 30 000-50 000, 30 000-100 000, 10 000-500 000 g mol-1, or at least around 100 000-200 000 g mol-1) from the low molar mass arabinoxylan oligosaccharides (AXOs).

The process combines pressurized hot-water extraction (PHWE), enzymatic treatment(s), and alternative membrane ultrafiltration(s) to isolate AX fractions from wheat bran with high purity and well-defined molecular structure. In one embodiment, the process comprises implementing membrane ultrafiltration to further purify the extracts. The extracts can be fractionated into a high molar mass fraction, containing mainly polymeric feruloylated arabinoxylan (F-AX), and a low molar mass fraction, containing mainly arabinose-containing xylo-oligosaccharides (AXOs). The isolated high molar mass and low molar mass fractions exhibit significant antioxidant properties in terms of radical scavenging activity, in comparison with AX from wheat endosperm and the alkaline extracts. This antioxidant activity can be attributed to the presence of ferulic acid covalently attached to the AX molecules.

In addition to this, the process can comprise different enzymatic treatments to further release AX from the unextractable residue. In particular, a combined action of an endo β-xylanase and a feruloyl esterase is capable of producing additional amounts of valuable F-AX oligosaccharides. The combined total yield of the integrated process design is higher than the yield obtained by alkaline extraction alone. The molecular composition of the different polymeric and oligomeric fractions has been characterised in detail. This knowledge provides the proof of concept for a potential upscaling of the extraction and fractionation process. Moreover, the process allows for successfully isolating of a broad range of fractions with well-defined molecular structures from cereals, e.g. from wheat bran. These fractions can be exploited for the preparation of films and gels with multi-functional activity, e.g. combining the inherent barrier and rheological properties with the potential antioxidant capacity. These materials can be used in a wide range of applications, from active packaging films to food stabilisers.

In a presently preferred embodiment, the isolated arabinoxylans (AXs) are predominantly feruloylated.

The present invention consequently relates to a process for isolating feruloylated arabinoxylans (AXs) from a cereal crop, such as from a cereal byproduct, comprising subjecting said cereal crop to pressurized hot water extraction and enzymatic treatment of the residual (non-extracted) fraction.

In said process, the isolated arabinoxylans (AXs) are selectively fractioned based on their molecular structure and inherent functionalities.

Typically, the cereal crop used in a process according to the present invention is selected from the group consisting of wheat bran, wheat grain, wheat flour, wheat straw, barley grain, Brewer's spent grain, barley flour, barley straw, rye grain, rye flour, rye bran, rye straw, oat grain, rice, corn, corn bran, rice bran, corn straw, corn husk, corn stower and oat bran.

The present invention also relates to feruloylated arabinoxylans (AXs) produced by a process according to the present invention as such and to the use of said feruloylated arabinoxylans (AXs) for the preparation of carbohydrate-based materials with functional properties, selected from the group consisting of films, hydrogels, active food packaging, prebiotics, bioactive compounds and texturizing agents.

In consequence, the present invention also relates to carbohydrate-based materials with functional properties, selected from the group consisting of films, hydrogels, active food packaging, prebiotics, bioactive compounds and texturizing agents comprising feruloylated arabinoxylans (AXs) produced and/or producible by the process according to the present invention.

FIGURE LEGENDS

FIG. 1: Molecular structure of cereal arabinoxylans, FIG. 1a The arabinose decorations may be further substituted by ester links in the C5 position by phenolic compounds, mainly ferulic acid (FerA). FIG. 1b water-extractable (WE-AX) and water-unextractable arabinoxylans (WU-AX).

Figure 2:
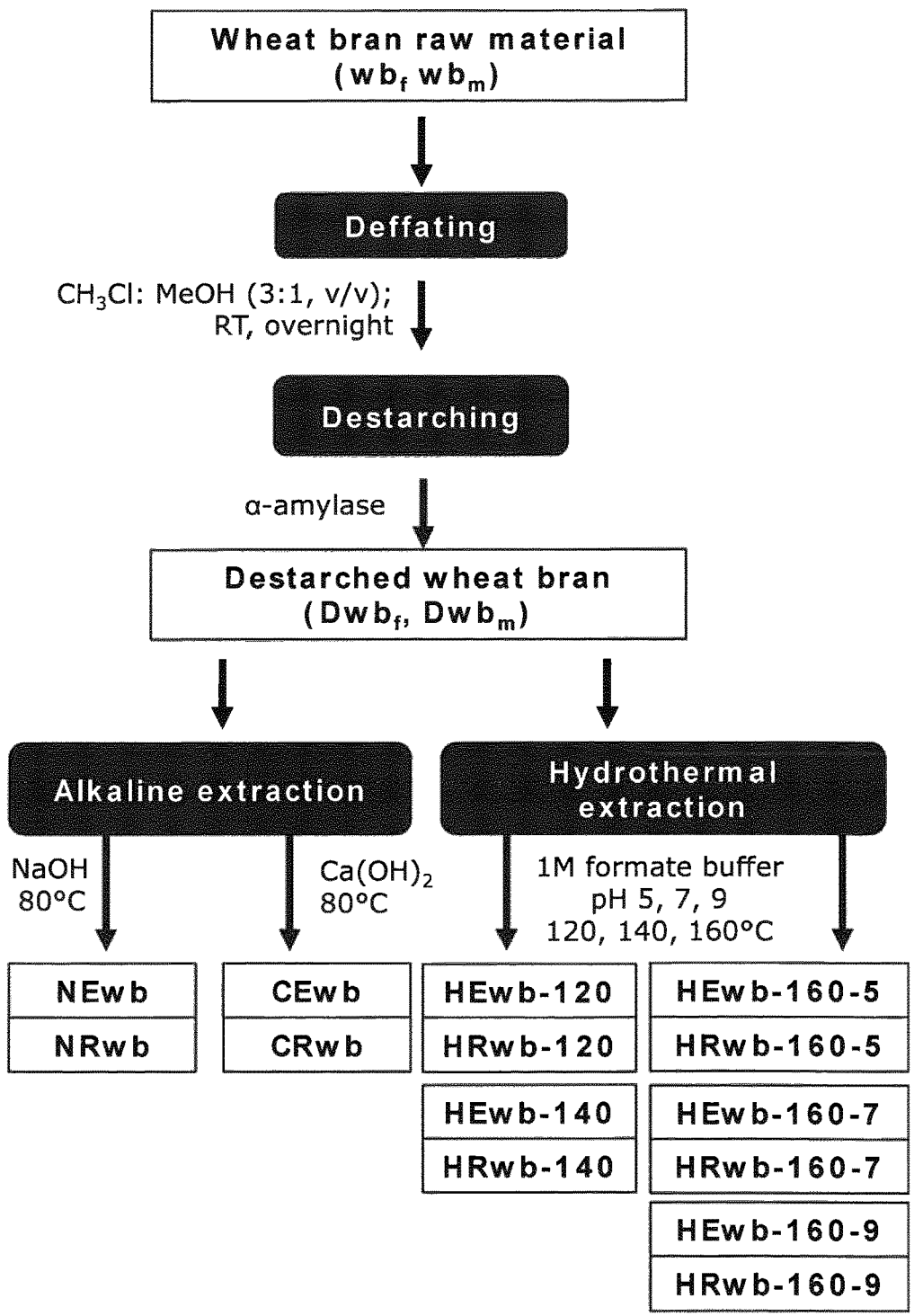

FIG. 2: Flow chart of the extraction treatments and fractions obtained thereof from wheat bran. Fractions: wbf (wheat bran fine grain), wb$_m$ (wheat bran medium grain), Dwbf (destarched and defatted wheat bran fine grain), Dwb$_m$ (destarched and defatted wheat bran medium grain), NE/Rwb (NaOH extract and residue from Dwbf), CE/Rwb (Ca(OH)2 extract and residue from Dwbf), HE/Rwb-120 (extract and residue from hydrothermal extraction at 120° C. pH5), HE/Rwb-140 (extract and residue from hydrothermal extraction at 140° C. pH5), HE/Rwb-160-5 (extract and residue from hydrothermal extraction at 160° C. pH5), HE/Rwb-160-7 (extract and residue from hydrothermal extraction at 160° C. pH7), HE/Rwb-160-9 (extract and residue from hydrothermal extraction at 160° C. pH9). Pictures: Wheat bran raw material and destarched: (A) wbf, (B) wb$_m$, (C) Dwbf, (D) Dwb$_m$. Alkaline extraction: (A) wbf, (B) Dwbf, (C) NEwb, (D) CEwb; Hydrothermal extraction: (A) wbf, (B) Dwbf, (C) HEwb-120, (D) HEwb-140, (E) HEwb-160-5, (F) HEwb-160-7, (G) HEwb-160-9.

Figure 3:
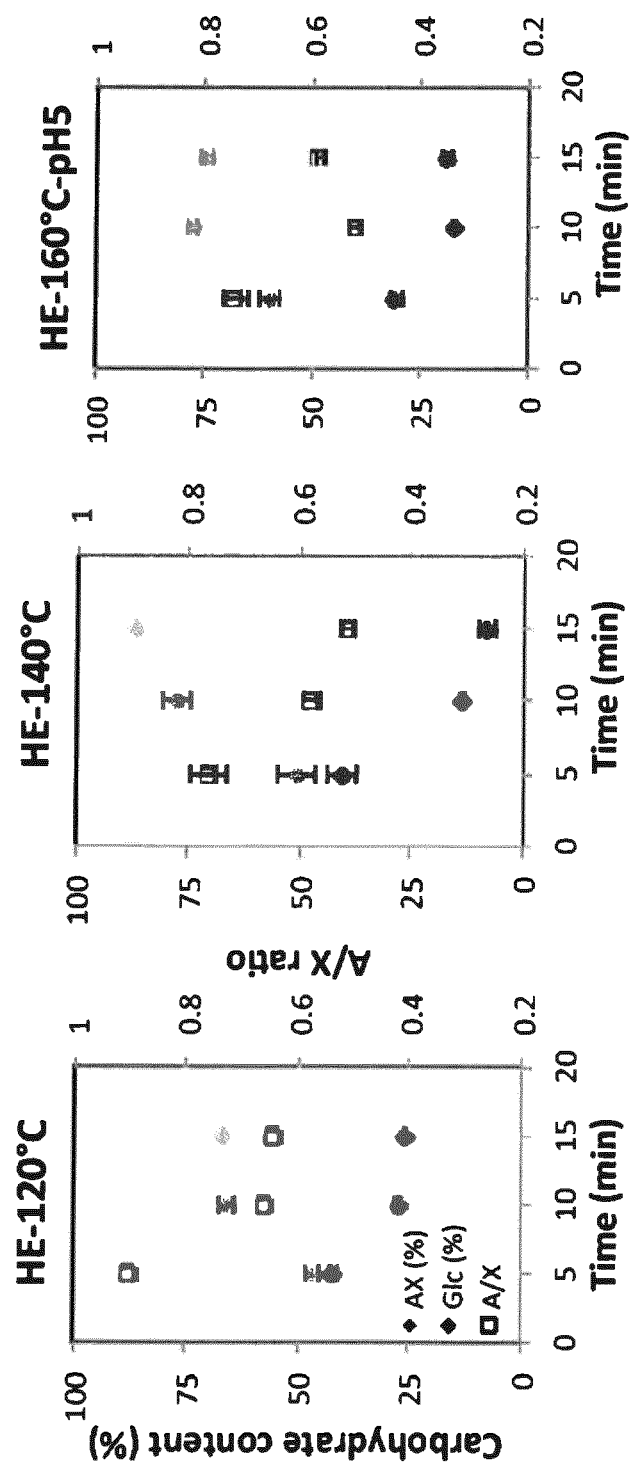

FIG. 3: Time evolution of the extracts after hydrothermal treatment for 5, 10 and 15 minutes: AX content (in % of total carbohydrate), Glc content (in % of total carbohydrate), A/X ratio.

Figure 4:
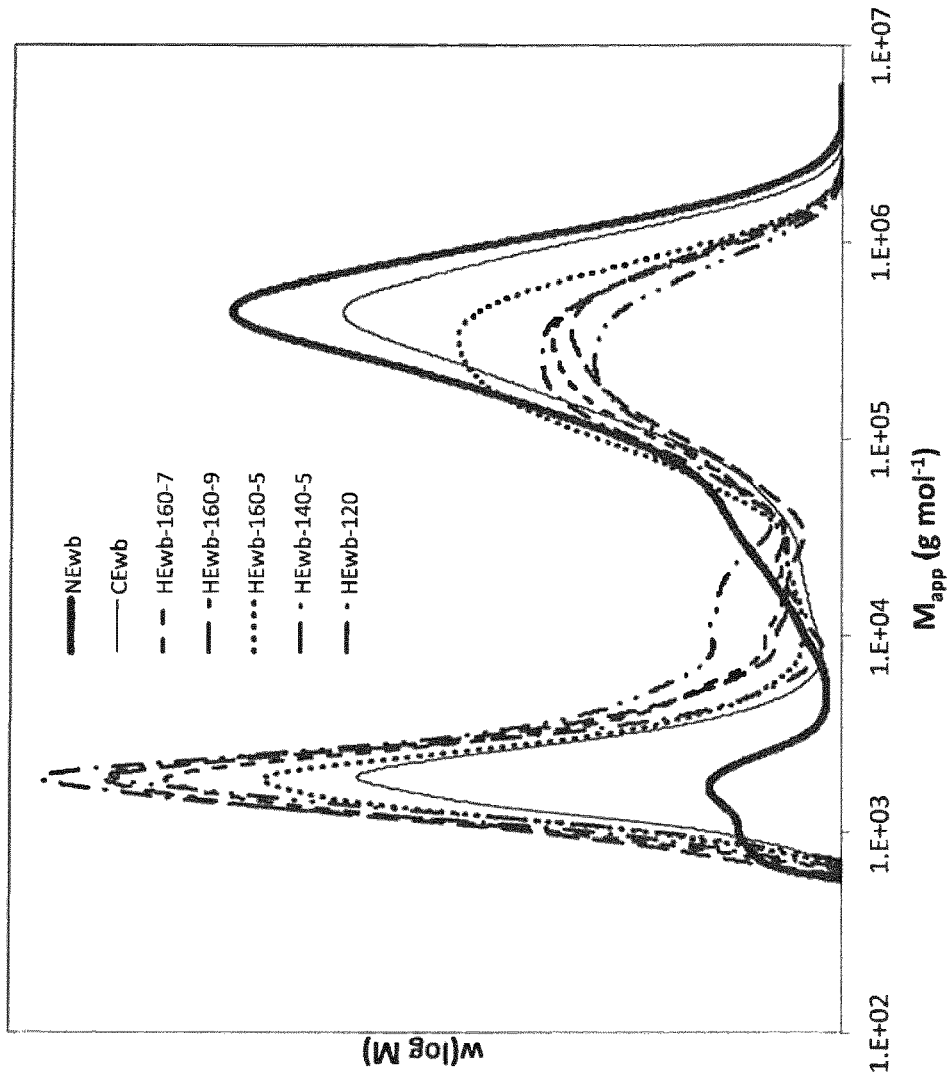

FIG. 4: Molar mass distributions and average molar masses of wheat bran from alkaline (NEwb and CEwb) and hydrothermal (HEwb-120, HEwb-140, Hewb-160-5, HEwb-160-7 and HE-160-9) extracts.

Figure 5:
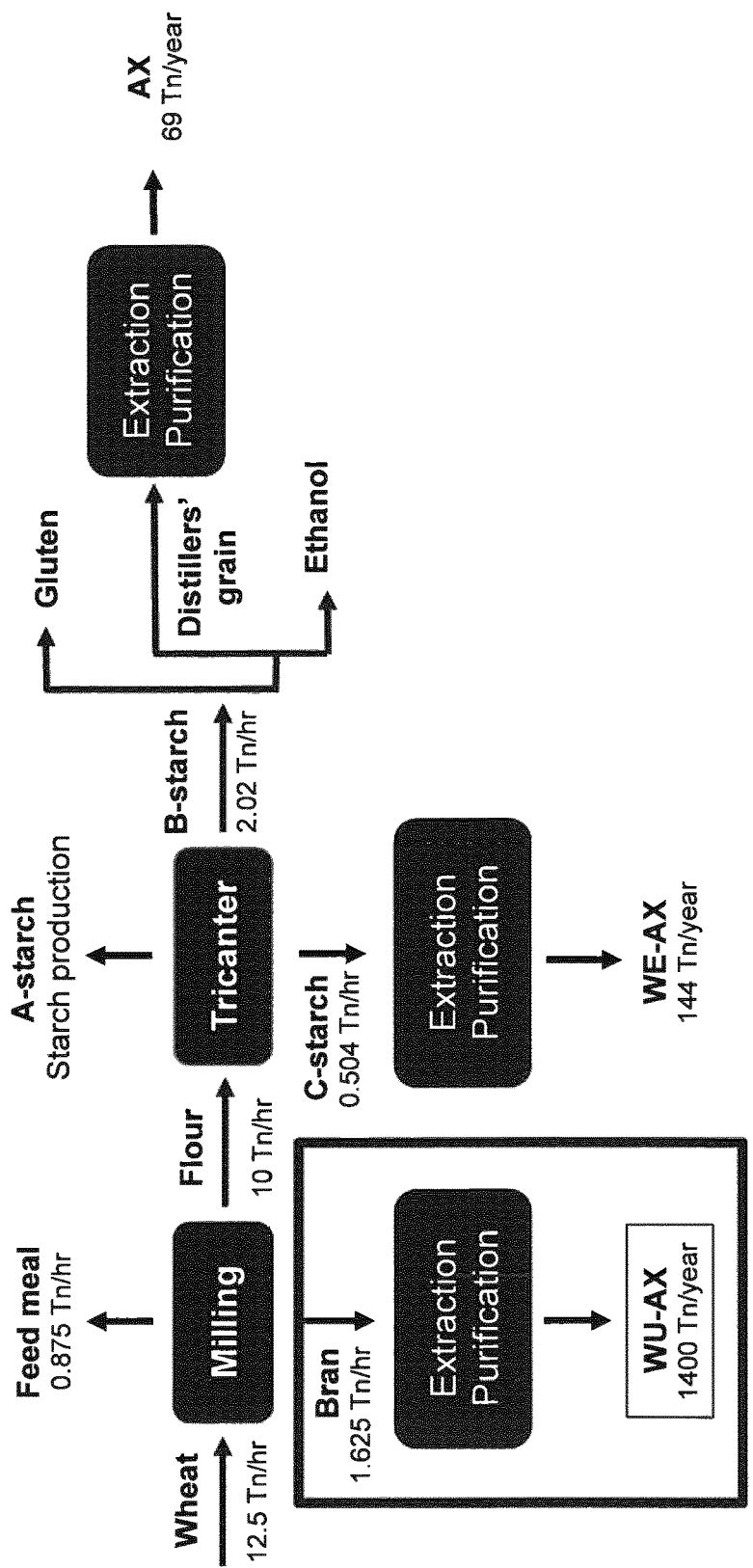
Figure 7A:
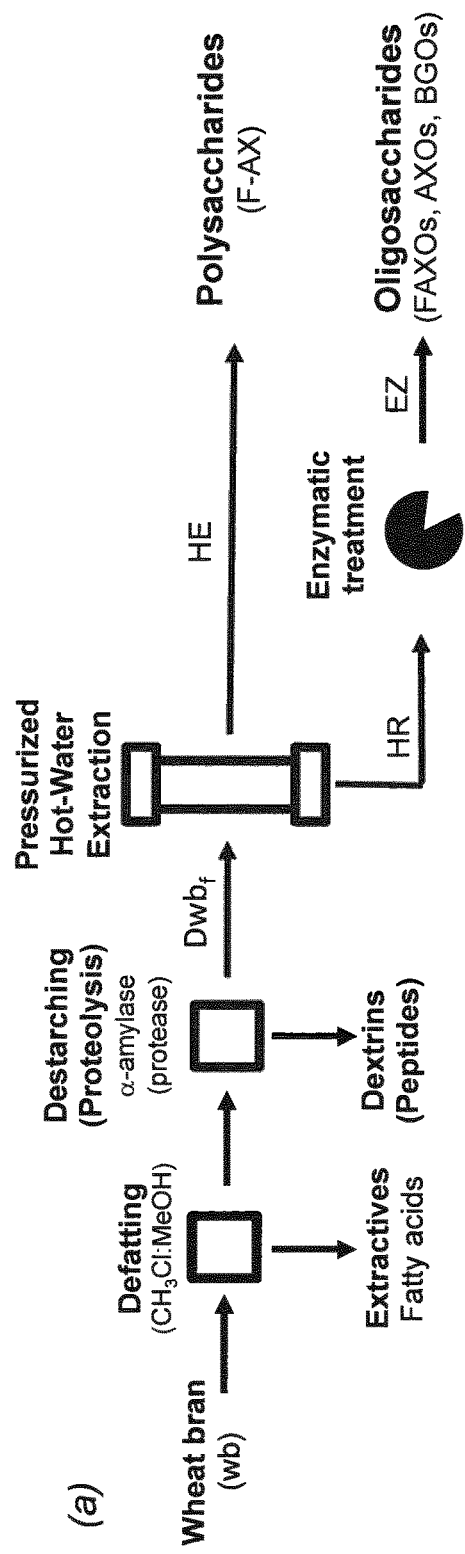
Figure 7B:
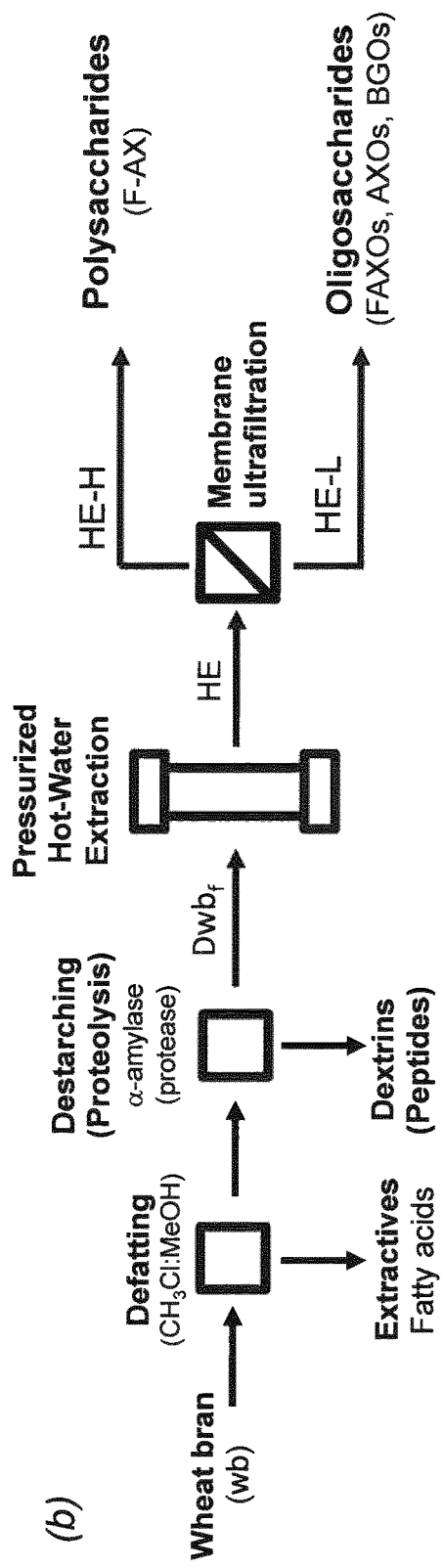
Figure 7C:
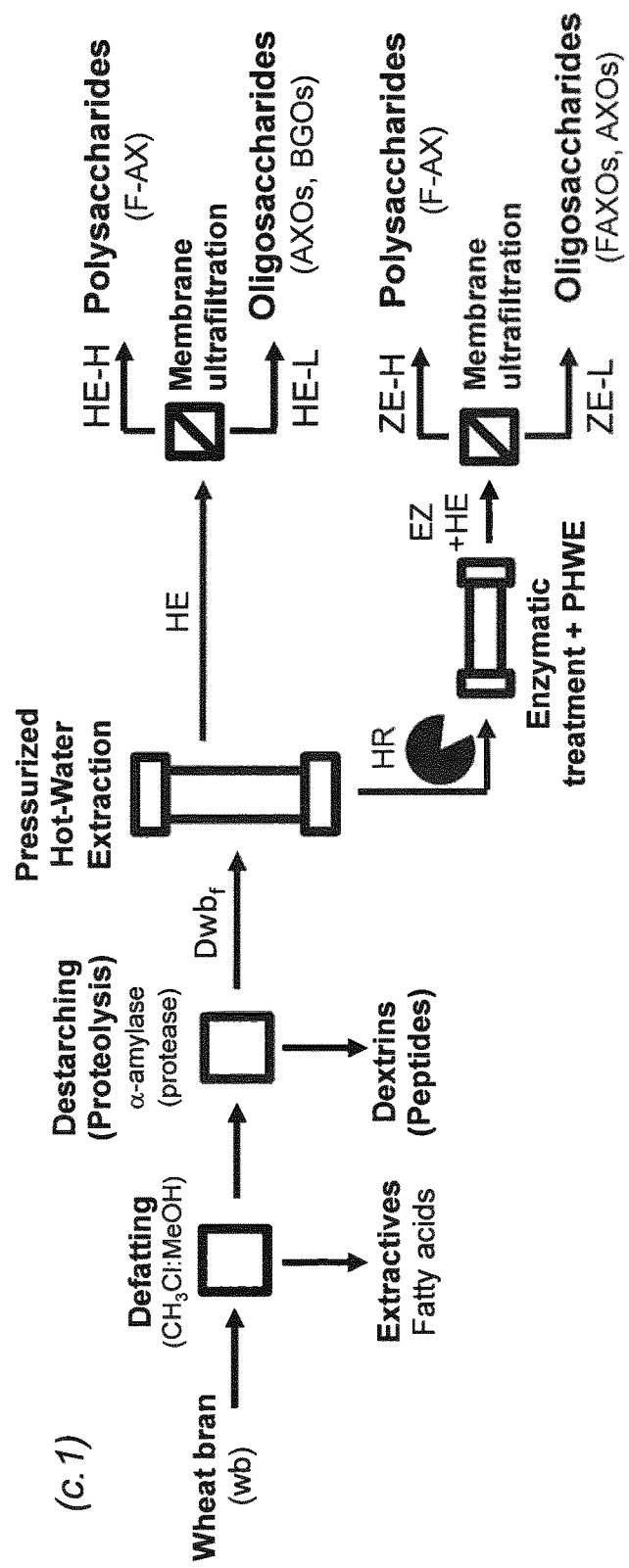
Figure 7D:
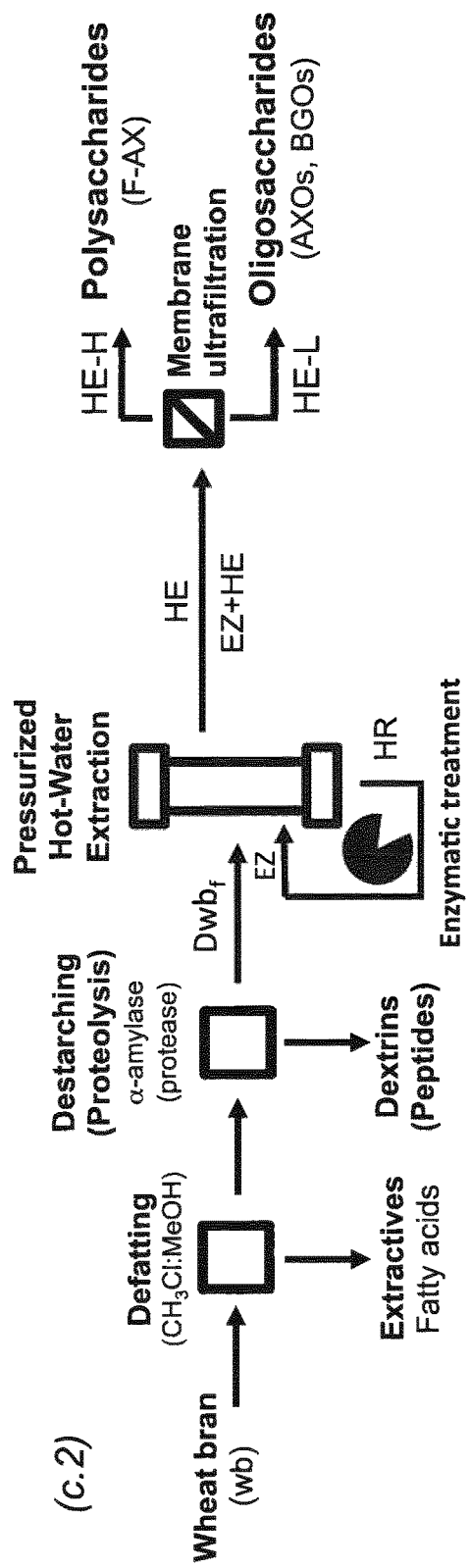

FIG. 5: Proposed material flows and arabinoxylan production from a Swedish wheat process plant for starch and bioethanol production (Lantmannen Reppe AB).

FIG. 6: Molecular structure of cereal arabinoxylans.
(a) Intramolecular substitution pattern in arabinoxylans:
(i) unsubstituted Xylp unit;
(ii) mono-substituted arabinoxylan with u-1,2-Araf;
(iii) arabinoxylan substituted with u-1,2-GlcA;
(iv) di-substituted arabinoxylan with u-1,2- and u-1,3-Araf;
(v) arabinoxylan substituted with u-1,2-4-O-methylGlcA;
(vi) arabinoxylan with ferulic acid coupled to a Araf substitute.
(b) Integrated bioanalytical platform for structural analysis of AX fractions at the different hierarchical levels.

FIG. 7: Design of a integrated bioprocess for the extraction and fractionation of biomolecules from wheat bran. Fractions: wbf (wheat bran fine grain), Dwbf (destarched and defatted wheat bran fine grain), HE (extract from pressurised hot-water extraction), HR (residue from pressurised hot-water extraction), HE-H (high molar mass fraction, retentate after membrane filtration), HE-L (low molar mass fraction, eluent after membrane filtration); EZ (fraction after enzymatic treatment of the residue), EZ+HE (fraction after enzymatic treatment of the residue and subsequent pressurized hot water extraction).

FIG. 8: Comparison of alkaline and pressurised hot-water (PHW) extraction: (a) gravimetric yields $g^{-1}$ (in % DW of Dwbf); (b) AX content (in mg $g^{-1}$ DW) determined after acid hydrolysis (TFA hydrolysis for the extracts, $H_2SO_4$ hydrolysis for the residues): extracts E (white), residues R (black) and dark; (c) ferulic acid content (in mg $g^{-1}$ DW) in the extracts E (white) and the residues R (Black).

Figure 9:
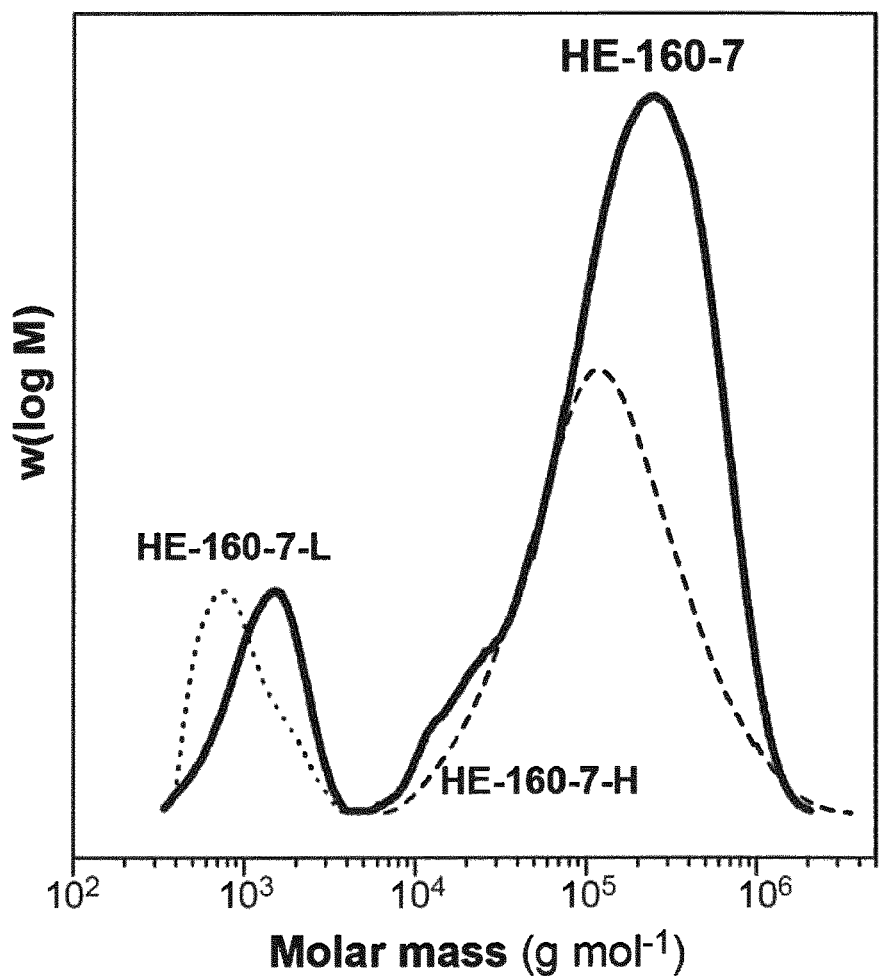
Figure 10:
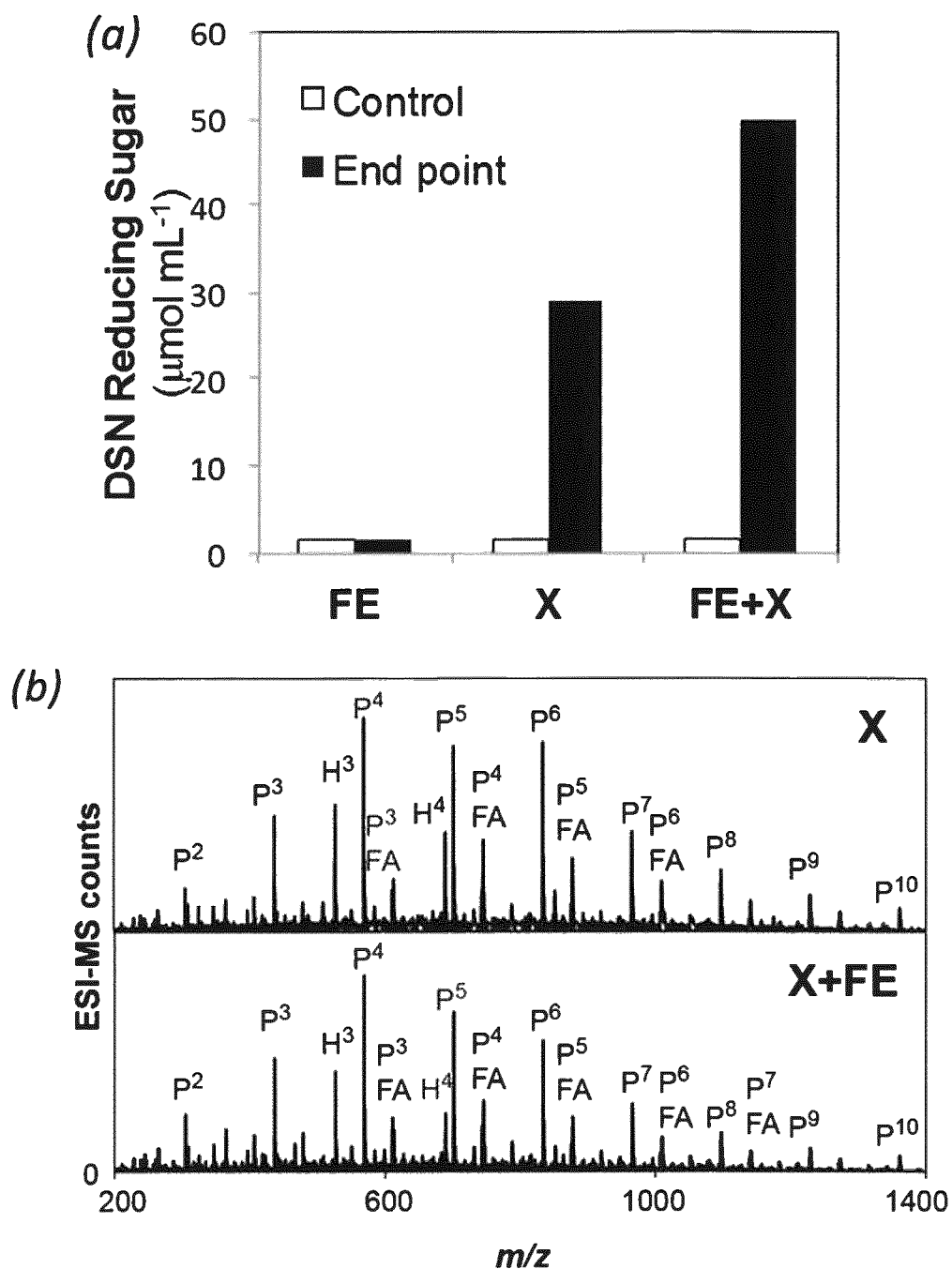

FIG. 9. Effect of membrane ultrafiltration on the molar mass distributions of the extracts: original extract after pressurized liquid extraction at 160° C. and pH 7 (HE-160-7, full line); retentate polysaccharide fraction with high molar mass after membrane ultrafiltration (HE-160-7-H, dashed line); eluted oligosaccharide fraction with low molar mass after membrane ultrafiltration (HE-160-7-L, dotted line);

FIG. 10. Enzymatic activity of selected xylan-acting enzymes on the residue after PHWE (HR-160-7). FE: feruloyl esterase; X: endo 3-xylanase; X+FE: combined action of feruloyl esterase and xylanase. (a) Released reducing sugars by DNS assay; (b) oligomeric mass profiling by ESI-MS. Assignment of the oligosaccharides. P: pentose (Xylp or Araf); FA: ferulic acid; H: hexose (Glc)

FIG. 11. Effect of a subsequent pressurized hydrothermal extraction on the residue (HR-160-7) after enzymatic treatment using selected xylan-acting enzymes: FE: feruloyl esterase; X: endo 3-xylanase; X+FE: combined action of feruloyl esterase and xylanase. (a) Extraction yields (in % dry weight of the residue): enzymatic treatment alone (EZ, in white), combined enzymatic treatment and subsequent PHW extraction (EZ+PHWE, in black); (b) AX composition (in mg g-1 dryweight) of the extracts after combined enzymatic treatment of the residue and subsequent pPHW extraction (EZ+PHWE).

Figure 12:
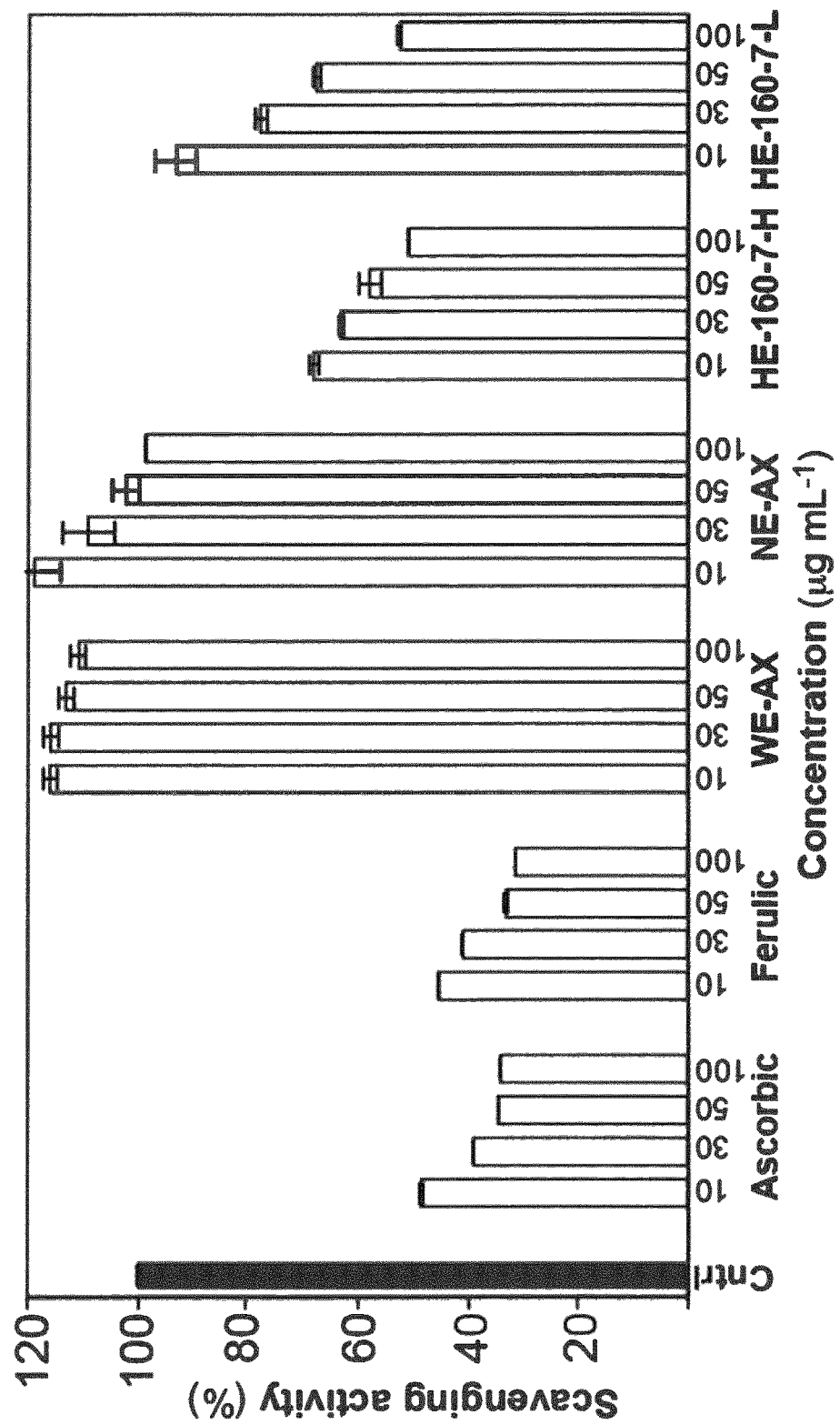

FIG. 12. Scavenging activity as measured using the DPHP test: control (DPHP); ascorbic acid; ferulic acid, WE-AX (endosperm AX, Megazyme standard); NE-AX (NaOH extracted AX); HE-160-7-H (high molar mass polysaccharide fraction from PHW extract at 160° C. pH7); HE-160-7-L (low molar mass oligosaccharide fraction from PHW extract at 160° C. pH7).

DETAILED DESCRIPTION OF THE INVENTION

Hemicelluloses constitute a rich cell wall polysaccharide fraction in cereal grains as non-starch polysaccharides. Cereal production generates high volumes of hemicellulosic byproducts, which represent a valuable renewable resource not fully exploited yet to their full capacity. E.g. wheat production plants (Lantmannen Reppe AB) have a potential flow of 1400 Tn/year of hemicelluloses comprising mainly arabinoxylans (AX) from wheat bran. The present invention valorizes polysaccharide as well as oligosaccharide fractions from wheat bran to produce carbohydrate-based materials (films and hydrogels) and additives with high added value in applications as active food packaging and texturizing agents. Different AX fractions are isolated from wheat bran, using scalable chemo-enzymatic and chromatographic processes. The structures at the molecular level of the isolated AX fractions are characterized using advanced analytical approaches. The extracted AXs are chemo-enzymatically modified to tailor their structures at the macromolecular level in terms of molar mass and substitution pattern. This allows for achieving desirable macroscopic properties (mechanical, barrier and rheological properties) and their functionalities as antioxidants and UV-absorbants in the AX-based films and hydrogels. These novel films and hydrogels are able to replace oil-based polymers and introduce new functionalities in applications as active food packaging and texturizing agents in cosmetic products, adhesives and binders. In one embodiment, new carbohydrate-based materials are obtained from wheat bran using "green" biochemical approaches, which offers new functionalities and applications to these cereal side products with high economic and environmental value.

In Sweden, the total cereal production for 2012 was 5.06 Million Tons, with wheat accounting for 45% of the production, barley for 33% and the rest being oats and rye[3]. Wheat is widely used for different food and industrial applications, such as flour, starch, and bioethanol. The generated byproducts (e.g. bran) are however still considered low value grades and are sold as animal feeds with a consistent market value linked to that of wheat flour. The valorization of such agricultural byproducts for material applications is therefore fundamental for a complete implementation of first generation biorefineries handling cereal grain waste streams.

The present invention discloses different scalable extraction procedures for the isolation of AX-rich fractions from cereal crops, such as cereal side products, e.g. wheat bran.

Pressurised hot water extraction is in one embodiment implemented at high temperatures in order to extract polymeric as well as oligomeric AX with intact ferulic functionalities. Different temperature and pH conditions are optimised to achieve high material yields. Moreover, compared to conventional alkaline extraction with sodium hydroxide (NaOH) and calcium hydroxide ($Ca(OH)_2$) the herein described pressurised liquid extraction procedure is superior in terms of yields and overall composition of the extracts and the residues. In one embodiment, different carbohydrate-active enzymes (CAZymes) are employed in combination with pressurised hot water extraction in order to increase the yields of extracted hemicelluloses and to isolate specific polysaccharide populations based on their molecular structure.

The molecular structures of the isolated fractions from wheat bran are characterized in detail using advanced glycomic approaches developed for different wood and cereal hemicelluloses. Carbohydrate composition (including Ara/Xyl ratio of the AX populations) and the content of phenolic compounds (FerA) are analyzed in the isolated fractions. The intramolecular linkage and substitution pattern is further monitored using enzymatic hydrolysis, chromatography and mass spectrometry. Finally the macromolecular architecture is analyzed by multiple-detection size-exclusion chromatography to provide meaningful molecular weight distributions and information on the hydrodynamic conformation in solution. This detailed molecular characterization enables a deep understanding of the pressurized hot water extraction process and the possibilities of the hemicellulose fractions for future material applications.

Hydrothermal treatment offers comparable extraction yields to conventional alkaline extraction preserving the feruloylated moieties in the AX backbone. In addition to this, the extract composition can be monitored through time during pressurized hot water treatment, which offers an indication of the extractability of the different polysaccharide components e.g. in wheat bran, based on their molecular structure. Interestingly, the hydrothermal residues contain significant amounts of water-unextractable AX with high ferulic acid content (feruloylated AX), which is assigned to a highly cross-linked material. Different enzymatic treatments are employed to release said cross-linked material from the insoluble residue into a water-extracted form, which constitutes a valuable fraction with interesting functionalities.

In the present context, the term AX with high ferulic acid content (feruloylated AX)" is employed to describe an isolated AX fraction with a ferulic acid content of 4 mg g$^{-1}$ (4 mg/g) such as 0.4%, 0.5, 0.6, 0.7, 0.75, 0.8, 0.85, 0.9, 0.95, 1, 1.5, 2, 2.5, 3, 3.5, 5, 10% or higher, covalently attached to the polysaccharide structure.

The presently disclosed production process allows the valorization of cereal by-products into carbohydrate-based materials using "green" biochemical approaches. In particular, arabinoxylans (AX) are extracted and fractionated e.g. from wheat bran, using scalable processes are structurally characterized by advanced bioanalytical approaches. These hemicellulose fractions can be chemo-enzymatically modified to tailor their properties for the design of films and hydrogels with high-added value in applications as active food packaging and texturizing agents respectively. These new materials themselves provide additional valuable functionalities as antioxidants and UV absorbents. The macroscopic properties (mechanical, barrier, and rheological properties) of these new bio-based materials are comparable and even better than existing fossil-based polymers. New AX-based materials can easily replace oil-based products in a wide plethora of applications.

The herein described production process provides a knowledge-based technological platform for the valorization of cereal byproducts into novel carbohydrate-based materials with tailored properties using "green" biochemical approaches. These novel materials have great potential in high-value applications as active film packaging and texturizing agents in diverse industries (cosmetic products, paint binders, adhesives). Valorization of different byproducts constitutes a fundamental task to reach an effective biorefinery process with near to zero waste generation.

In addition, the process also offers a means to gain valuable knowledge about the molecular structure of the polysaccharide fractions from wheat, which in itself contributes to a better understanding of the cereal overall structure and how to optimize existing biotechnological processes with lower production costs.

New products are obtained comprising residual polysaccharide fractions that traditionally have not been optimally used, expanding their applicability range. Novel carbohydrate-based materials are envisioned with high-added value, which are able to substitute traditional petrochemical-based materials. The potential of these materials is based on the inherent properties of the constituent polysaccharides (mechanical strength, gel-forming ability, bioactivity), their additional functionalities as antioxidants and UV-absorbents, and their sustainability. What is more, AX-based materials obtained by the herein disclosed production process arise from renewable resources, they can be processed using clean technology, and they present no harmful effects during their entire life cycle, contributing to a sustainable development and to mitigate climate change effects.

In the experimental section, different industrially scalable extraction procedures are evaluated for the isolation of arabinoxylan (AX) rich fractions from wheat bran. Conventional alkaline extraction with sodium hydroxide and calcium hydroxide was compared with hydrothermal extraction with pressurized hot water in terms of yields and overall composition of the extracts and the residues. Different experimental conditions including temperature, pH and time were assessed for the hydrothermal extraction. The general composition of two wheat bran raw materials with fine and medium granulometry was evaluated indicating a high content of arabinoxylan. The carbohydrate content and AX composition was however different in the two raw materials. Alkaline extraction with NaOH offered high yields of polymeric AX with high molar mass; however, the high pH values caused the cleavage of phenolic acid functionalities from the AX fractions. Hydrothermal treatment at 160° C. offered comparable AX extraction yields with somewhat smaller molar masses than the alkaline extracts.

The proposed process is easily scaled up by utilizing a pressurized vessel with the desired volume (30-200 L) capable of handling the pressure of subcritical water at the extraction temperature (see Table 1). For example, for the proposed extraction temperature of 160° C., a pressurized vessel at 10 bar offers the conditions for the pressurized hot water extraction in large scale. The fractionation of the extracts into a high molar mass polysaccharide fraction and a low molar mass oligosaccharide fraction can be as well upscaled using conventional membrane ultrafiltration with the same membrane cut-off as the one used in Experiment 2.

TABLE 1

| T (° C.) | Pressure (bar) |
|---|---|
| 100 | 1.01 |
| 120 | 1.99 |
| 140 | 3.62 |
| 160 | 6.18 |
| 180 | 10.03 |

The present invention therefore relates to a process for producing a hemicellulose fraction from a cereal crop, such as from a cereal byproduct, comprising subjecting said cereal crop to pressurized hot water extraction and enzymatic treatment at a temperature of between 140-160° C., such as between 140-150, 145-155, or 150-160° C., or of at least 140, 150, 155, 156, 157, 158, 159 or 160° C., at a pH between pH5-7.5, such as between pH5-5.5, 5-6, 6-6.5 or 6.5-7.0, or at a pH of at least 5.0, 5.5, 6.0, 6.5, 6.6, 6.7, 6.8, 6.9, 7.0, 7.1, 7.2, 7.3, 7.4 or 7.5.

In one embodiment, the (hydrothermal) pressurized hot water extraction in step a) is performed at a temperature of at the most 160° C. in a pH of at the most pH7.0.

In another embodiment, the (hydrothermal) pressurized hot water extraction in step a) is performed at a temperature of at the least 158° C., such as at the least 159 or 160° C. in a pH of at the least pH6.7, such as at the least pH6.8, 6.9 or 7.0.

The evolution of the extract composition during pressurized hot water treatment offered an indication of the extractability of the different polysaccharide components in wheat bran based on their molecular structure. Interestingly, the hydrothermal residues contained significant amounts of water-unextractable AX with high ferulic acid content (feruloylated AX) that constitute a valuable fraction with interesting functionalities. Further enzymatic treatments are implemented to isolate such feruloylated AX fractions from the water-unextractable residues. All the extracted fractions contain significant amounts of lower molar mass impurities and glucan populations (probably β-glucans). Purification treatments by membrane ultrafiltration and enzymatic hydrolysis can therefore be implemented when required to achieve extracted AX fractions with higher purity. In conclusion, a broad palette of AX fractions with high purity and well-defined molecular structure can be obtained for the preparation of functional AX-based materials.

Arabinoxylan (AX)

Arabinoxylan (AX) is the most abundant hemicellulose in cereals as part of the grain and the straw. AXs, as other plant hemicelluloses, possess a very complex molecular structure in terms of the virtually infinite possibilities for substitution patterns along the sugar backbone, and their (poly)dispersity in terms of molar mass distributions. This heterogeneous structure varies not only from one cereal species to another, but also in the different tissues (FIG. 2a). Cereal AXs consist of a backbone of 1,4-β-D-xylopyranose (Xylp) units, which are mainly substituted by arabinofuranosyl units (Araf) in the α-1,2 and/or α-1,3 positions to different extents and intramolecular distributions, depending on the biological source and tissue[5,6]. The Xylp units may be substituted to a lower extent by 1,2-α-D-glucuronic acid, either unsubstituted (GlcA) or methylated in the C4 position (4-O-Me-GlcA)[7]. Finally, the arabinose decorations may be further substituted by ester links in the C5 position by phenolic compounds, mainly ferulic acid; these phenolic compounds can dimerize with other ferulic acid moieties in other arabinoxylan molecules, creating a complex crosslinked covalent structure in some tissues[8]. This molecular heterogeneity has a great impact on the extractability of these hemicelluloses during industrial processes and on their macroscopic properties (e.g. solubility, rheological, film forming and mechanical properties), which are fundamental for their material applications.

From a technological point of view, the arabinoxylans from different cereals and tissues have been traditionally classified in water-extractable arabinoxylans (WE-AX) and water-unextractable arabinoxylans (WU-AX), depending on their potential aqueous extractability at room temperature. Again, the content of each arabinoxylan fraction and its macromolecular structure depends widely on the cereal source and the tissue. There is broad variability in the literature about the availability and composition of each arabinoxylan fraction in each cereal and tissue (Table 1). As a rule of thumb, WE-AXs are mainly present in the cereal endosperm and are moderately substituted with arabinose. On the contrary, WU-AXs are predominant in the cereal bran representing approximately 95% of the total estimated AX content. WU-AXs show great heterogeneity in their structure[9,10], with fractions containing very divergent Araf substitution patterns and further decorated with GlcA and ferulic acid, which contribute to crosslinking with other arabinoxylan molecules and other cell wall components. This project will tackle these challenges by implementing integrated physico-chemical and enzymatic extraction procedures to maximize the yield of WU-AX extracted from wheat bran and by developing an analytical platform for the detailed characterization of the molecular structure of such extracted AX fractions.

Wood and cereal xylans have shown great potential for the production of biopolymeric films for packaging applications. Several efforts have been already made for the application of cereal AXs as packaging films[11-16]. These studies have mainly used commercial refined water-soluble arabinoxylan (WE-AX) fractions with moderate Araf substitution degree, to prepare films, with and without the addition of plasticizers, showing good oxygen barrier properties but limited water sensitivity and mechanical properties[17]. AX films have also been reinforced with cellulose nanostructures in order to improve their mechanical properties 18-20.

Moreover, AXs have very interesting rheological properties and can form strong gels under the action of certain oxidizing agents, with neutral odour and high stability[8]. Up to this point, there are four patents for the exploitation of wood and cereal hemicelluloses as films with oxygen and moisture barrier properties[21-24], but in all cases they rely on chemical modification and on the introduction of external additives. Different methods are available for the extraction and production of AX oligosaccharides from cereal bran to be used as food ingredients (e.g.[25,26]). However, no technique is available yet on the fractionation of high molar mass arabinoxylans from wheat bran and their application for films and texturizing agents as the main components.

The present invention for the first time allows the production of different isolated AX fractions from wheat bran and their use for the preparation of films and hydrogels with tailored molecular structure, targeting their application as active food packaging and texturizing agents. These texturizing agents can find wide applications as replacement of acrylic gels as binders in adhesive and coatings, or as thickening agents in cosmetic formulations. Not only the Araf but also the GlcA and ferulic acid functionalities in the AX fractions are obtained and evaluated herein. The Araf and GlcA substitutions influence the film-forming, barrier, and rheological properties of the AX fractions, which can be tailored for the preparation of films and hydrogels. Moreover, the uronic and ferulic acid groups can be used for further chemical and enzymatic crosslinking, which can increase the mechanical and rheological properties of the materials. Finally, the ferulic acid moieties can introduce antioxidant and UV-absorbent properties, which will provide high value to the packaging film and texturizing gel products.

TABLE 2

Composition and relative amounts (in % dry weight) of AX and β-glucans in different cereal tissues.

| | | Arabinoxylans (AX) | | Mixed-linkage |
| --- | --- | --- | --- | --- |
| | Cereal tissue | WE-AX | Total | β-glucans |
| Wheat | Grain6,27 | 0.5% | 6% | 0.4-1.5%[28] |
| | Endosperm (flour)6,29 | 0.5% | 2.2% | |
| | Bran6,27 | 0.8% | 20-33% | |
| | Straw30-32 | 20-25% | 3-5% | |

TABLE 2-continued

Composition and relative amounts (in % dry weight) of AX and β-glucans in different cereal tissues.

| | | Arabinoxylans (AX) | | Mixed-linkage |
|---|---|---|---|---|
| | Cereal tissue | WE-AX | Total | β-glucans |
| Barley | Grain[27] | 0.5-1% | 4-7% | 2.5-11.3%[28] |
| | Brewers' spent | 0.5% | 13.5% | |
| | Straw[33] | | 15-25% | 3-7% |
| Rye | Grain34,35 | 2.4-8% | 7-12% | 2-3%[28] |
| | Flour34,35 | 2.5% | 3.5-9% | |
| | Bran[34] | 2.1% | 12.6% | |
| | Straw[36] | | 22-25% | |
| Oats | Grain[27] | 0.2% | 2.7% | 2.2-7.8%[28] |
| | Bran[27] | 0.33% | 3.5% | |

The WU-AX content can be estimated as the difference between the total AX content and the WE-AX.

REFERENCES

1. A ElMekawy, L Diels, H De Wever, D Pant. *Environm. Sci. Techn.* 2013 47, 9014,
2. M S Izydorczyk, C G Biliaderis. *Carbohydr. Polym.* 1995 28, 33,
3. L Saulnier, P-E Sado, G Branlard, G Charmet, F Guillon. *J Cereal Sci.* 2007 46, 261,
4. A Ebringerova, Z Hromadkova, T Heinze. in *Polysaccharides I Adv. Polym. Sci.* 2005 186, 1.
5. G Niño-Medina, E Carvajal-Millan, A Rascon-Chu, J Marquez-Escalante, V Guerrero, E Salas-Munoz. *Phytochem. Rev.* 2010 9, 111,
6. J M Lawther, R Sun, W B Banks. *J. Agricult. Food Chem.* 1995 43, 667,
7. Z Merali, J D Ho, S R A Collins, G LeGall, A Elliston, A Kasper, K W Waldron. *Biores. Techn.* 2013 131, 226,
8. M S lzydorczyk, J E Dexter. *Food Res. Int.* 2008 41, 850,
9. M Aguedo, C Fougnies, M Dermience, A Richel. *Carbohydr. Polym.* 1 2014 105, 317,
10. Aguedo, M.; Fougnies, C.; Dermience, M.; Richel, A. *Carbohydrate Polymers* 2014, 105, 317-324.
11. Saeman, J. F.; Moore, W. E.; Mitchell, R. L.; Millett, M. A. *Tappi Journal* 1954, 37, 336-343.
12. Comino, P.; Collins, H.; Lahnstein, J.; Beahan, C.; Gidley, M. J. *Food Hydrocolloids* 2014, 41, 219-226.
13. Sassaki, G. L.; Souza, L. M.; Serrato, R. V.; Cipriani, T. R.; Gorin, P. A. J.; Iacomini, M. *Journal of Chromatography A* 2008, 1208, 215-222.
14. Immerzeel, P.; Falck, P.; Galbe, M.; Adlercreutz, P.; Nordberg Karlsson, E.; Stålbrand, H. *LWT—Food Science and Technology* 2014, 56, 321-327.
15. Schooneveld-Bergmans, M. E. F. *Wheat bran glucuronoarabinoxylans biochemical and physical aspects*. Proefschrift Wageningen, Nederlands., 1997.
16. Stevenson, L.; Phillips, F.; O'Sullivan, K.; Walton, J. *International Journal of Food Sciences and Nutrition* 2012, 63, 1001-1013.
17. Bilgicli, N.; Ibanoglu, S. *J Food Eng* 2007, 78, 681-686.
18. Lantmännen Reppe AB.
19. Haskå, L.; Nyman, M.; R., A. *Journal of Cereal Science.* 2008, 48, 768-774.
20. Tkachuk, R.; Irvine, G. N. *Cereal Chemistry* 1969, 46, 206-218.
21. Di Lena, G.; Vivanti, V.; Quaglia, G. B. *Nahrung* 1997, 41, 285-288.
22. Zhou, S.; Liu, X.; Guo, Y.; Wang, Q.; Peng, D.; Cao, L. *Carbohydrate Polymers* 2010, 81, 784-789.
23. Gruppen, H.; Hamer, R. J.; Voragen, A. G. J. *Journal of Cereal Science* 1991, 13, 275-290.
24. Bergmans, M. E. F.; Beldman, G.; Gruppen, H.; Voragen, A. G. J. *Journal of Cereal Science* 1996, 23, 235-245.
25. (1) Aguedo, M. et. al. Carbohydrate Polymers 2014, 105, 317-324.
26. (2) Saeman, J. F. et. al. Tappi Journal 1954, 37, 336-343.
27. (3) McKee, L. S. et. al. Biotechnology for Biofuels 2016, 9, 1-13.
28. (4) Comino, P. et al. Food Hydrocolloids 2014, 41, 219-226.
29. (5) Brand-Williams, W. et. al. LWT—Food Science and Technology 1995, 28, 25-30.
30. (6) Pussayanawin, V. et. al. Journal of Agricultural and Food Chemistry 1988, 36, 515-520.

EXPERIMENTS

Experiment 1

Objective of the Project

The overall objective of the project is the valorisation of arabinoxylans from wheat bran into carbohydrate-based materials using "green" biochemical approaches. Arabinoxylans from wheat bran are extracted and fractionated using scalable processes and the AX rich fractions are structurally characterized by bioanalytical approaches. These fractions are used for the design of films and hydrogels with high-added value in applications as active food packaging and texturizing agents respectively. These new AX-based materials can provide additional valuable functionalities as antioxidants and UV absorbents.

Hypothesis

Conventional alkaline extraction is the standard procedure to isolate arabinoxylans from cereal streams. However, high pH values during extraction are known to alter the molecular structure of the fractions and remove part of the decorations from the AX extracts, which are valuable for their further material applications. Hydrothermal extraction with pressurized hot water constitutes a milder extraction procedure for hemicelluloses from biomass, thus preserving the native molecular structures of the polymeric populations. The efficiency (yield) and composition of the AX fractions extracted from wheat bran by alkaline and hydrothermal extractions are compared and different experimental conditions (pH, temperature, time) are assessed for the latter.

3. Materials and methods.

3.1 Materials

Wheat bran was provided by Lantmannen with two different particle sizes: fine (wbf) and medium granulometry (wb$_m$) (FIG. 2). All chemicals, analytical standards and reagents were from Sigma-Aldrich. α-Amylase porcine pancreatic was purchased from Sigma-Aldrich. Pholin Ciocalteau Phenol reagent was from Merck. Spectra/Por 1 and 3 Dialysis Membrane, 6-8 kD and 3.5 kDa MWCO were purchased from SpectrumLabs.

3.2 Extraction Protocols

The combined extraction procedures and the different materials and fractions obtained are summarized in FIG. 2.

3.2.1 Defatting and Total Fat Content

The samples wbf and wb$_m$ were defatted and their total fat content was determined according to Folch method with some modifications.[1] Briefly, 5 g of dry sample were extracted with 50 mL of a mixture of chloroform ($CHCl_3$) and methanol (MeOH) (2:1, v/v) overnight under stirring. The extract was filtrated on a pleated paper filter, and washed with the same mixture. The extract was placed in a funnel and 20 mL of NaCl 0.58% were added, stirred and left to settle. The organic phase was recovered, dried under a constant airflow at 35° C. and left under vacuum for 15 min prior to gravimetrical determination.

3.2.2 Destarching

The bran was enzymatically destarched with α-amylase. In brief, the bran was suspended in 0.01 M phosphate buffer with 100 mM KCL (pH 7.5) in a ratio of 1:10 (w/v) and boiled for 5 min to gelatinize the starch granules. The samples were equilibrated at 40° C. and incubated with α-amylase (2 U/mg of carbohydrate) for 1 h at 40° C.; a second incubation was performed with a full dose of α-amylase for further 30 min. The polysaccharides were precipitated by addition of four volumes of cold absolute ethanol at −8° C. overnight and centrifuged (1500 g, 5 min). The supernatant was removed, and the remaining precipitate was washed with cold absolute ethanol (3 times) and water, centrifuging between washes, prior to freeze-drying. Starch removal was verified under the microscope by iodine staining with 1% iodine (w/v), 2% potassium iodide (w/v). The total starch content was determined gravimetrically before and after the α-amylase treatment.

3.2.3 Alkaline Extraction

Defatted and destarched fine wheat bran (Dwbf) was submitted to two different alkaline extraction methods using either 0.5M NaOH or Ca(OH)2 concentrated solution at 80° C. for 16 h using a ratio of 1:8 (w/v). The recovered supernatants and the residues were neutralized with addition of acetic acid and dialyzed against tap water for 48 h using a 3.5 kDa MWCO dialysis membrane. The alkaline extracts and residues were concentrated and freeze-dried, in order to give the respective yields relative to the dry weight.

3.2.4 Hydrothermal Extraction by Pressurized Hot Water

Hydrothermal extraction of Dwbf was performed by pressurized hot water using a Dionex™ ASE™ 350 Accelerated Solvent Extractor from Thermo Scientific™. Three different temperatures were tested: 120, 140 and 160° C. at pH 5.0, and pH 7.0 and 9.0 were also tested at 160° C. 1M sodium formate buffer was used as solvent and the pH was corrected by addition of 1M formic acid, the volume of solvent used for each extraction was 30 ml. 1 g of Dwbf was used in each condition, and the extractions were done in three subsequent cycles of 5 min, resulting in 3 extracts and 1 residue for each one of the tested conditions. In order to obtain the yields all the extracts and residues were dialyzed against tap water with a 6-8 kDa MWCO membrane for 72 h and freeze-dried.

3.3 Characterization of the Extracted Fractions 3.3.1 Monosaccharide Content and Composition The monosaccharide content and composition of the wheat bran raw material and the subsequent fractions was analyzed by acid hydrolysis followed by high-pH anion exchange chromatography with pulsed amperometric detection (HPAEC-PAD). Sulfuric hydrolysis was performed using the conditions originally reported by Saeman.[2] In brief, 1-5 mg of freeze-dried material was swelled with 72% $H_{2SO4}$ for 3 hr at room temperature and subsequently diluted to 1M $_{H2SO4}$ by adding Milli-Q water. The samples were further hydrolyzed at 100° C. for 3 hr, cooled down and diluted until further HPAEC-PAD analysis. TFA hydrolysis was performed with 1-5 mg of freeze-dried material with 2 M TFA at 121° C. for 3 hr. A 100 uL aliquot was taken from the hydrolysates, vacuum dried and redissolved in 1 mL Milli-Q water until further HPAEC-PAD analysis.

The hydrolysed monosaccharides were analysed by high-pH anion exchange chromatography with pulsed amperometric detection (HPAEC-PAD) on an ICS3000 system (Dionex, Sunnyvale, Calif.) using a Dionex CarboPac PA1 column maintained at 30° C. at a flow rate of 1 mL min$^{-1}$. Different gradients were employed for the detection and quantification of the neutral monosaccharides and uronic acids.

3.3.2 Phenolic Content and Composition

The phenolic acid content and composition was determined by saponification, silylation and GC-MS. 5 mg of each sample (in duplicate) were saponified with 300 μL of 2 M NaOH overnight at room temperature in the dark. The samples were then acidified (to pH 3.0) with 55 μL 12 M hydrochloric acid and internal standard (4-hydroxybenzoic acid—5 μg) was added. The phenolics were extracted with 1 ml ethyl acetate, nitrogen dried, and then silylated with 50 μL N—O-bis (trimethylsilyl acetamide) at 100° C. for 5 min. The derivatised phenolics were resuspended in dichloromethane and injected onto a GC-MS[3].

3.3.3 Amino Acid Content and Composition

The samples (10 mg dry weight) were hydrolysed with 6 M HCl at 100° C. for 20 h, with 1% phenol (v/v). The hydrolysed and freeze-dried samples were dissolved in aqueous-methanolic solution (200 μl; 1.5:8.5, v/v) containing 0.6N HCl and 0.1% of phenol (v/v), heated at 100° C. for 15 min, and evaporated under a N2 stream. The residue was derivatised with pyridine-methanol-acetic anhydride (300 μl, 1:1:4, v/v) at 100° C. for 60 min, into amino acid methyl esters (aaMAs). The products were directly analysed by GC-MS[4].

3.3.4 Fat Content and Composition

The main fatty acids were esterified and then quantified by GC-MS.[4] Briefly, to an aliquot of the extract 1 mL of 2M TFA was added, and the hydrolysis was performed at 100° C., for 8 h. The hydrolysed samples were dissolved in 0.5N NH$_4$OH (100 μl), held at room temperature for 10-15 min in reinforced hydrolysis tubes with Teflon lined screw cap vessels. NaBH4 (1 mg) was added, and the solution was maintained at 100° C. for 10 min. The product was dried, washed with acetic acid (100 μl) and methanol (×2), and further dried under N2 in a fume hood. The residue was treated with 0.5M HCl in MeOH (200 μl) at 100° C. for 15 min, followed by evaporation under a mild N2 stream in a fume hood, giving rise to fatty acid methyl esters. Acetylation was performed in pyridine-Ac2O (200 μl; 1:1, v/v), heated for 30 min at 100° C. The products were added to aq. 2% CuSO4, and extracted with CHCl3, which was evaporated using a stream of N2 and resuspended in ethyl acetate for GC-MS analysis.

3.3.5 Molar Mass Distributions by SEC

The molar mass distributions of the extracted arabinoxylans from wheat bran were analysed by size exclusion chromatography (SECcurity 1260, Polymer Standard Services, Mainz, Germany) coupled to a refractive index detector (SECcurity 1260, Polymer Standard Services, Mainz, Germany) thermostatted at 45° C. The extracted fractions were dissolved directly in the SEC eluent consisting of dimethyl sulfoxide (DMSO, HPLC grade, Scharlab, Sweden) with 0.5% w/w LiBr (ReagentPlus) at 60° C. The concentrations were adjusted between 0.5-2 gL$^{-1}$ for optimized detection signal. SEC analyses were performed with a flow rate of 0.5 mL min$^{-1}$ at 60° C. using a column set consisting of a GRAM PreColumn, 30 and 10000 analytical columns (Polymer Standards Services, Mainz, Germany). Calibration of the SEC separation was performed using pullulan standards provided by Polymer Standards Services (PSS, Mainz, Germany).

4. Results

4.1 Raw Wheat Bran and Initial Pre-Treatments (Destarching and Defatting)

Carbohydrates are the main components of bran, with contents that oscillate between 40-60% in different industrial wheat brans.[5,6] Proteins account for approximately 15-20% (DW) of the total bran composition[5,6], whereas expected fat content can oscillate between 3-5%.[1,6] Total phenolic acid accounts for 1-2% of the total bran, whereas lignin can occur between 48%.[6] Other components are phytic acid, which can account for 3-6% of the total dry weight[7,8], and ash content, which oscillates between 4-6%.[5,6,9,10] Phytic acid may be an interesting fine chemical to isolate from wheat bran, since it has antioxidant properties. The general composition of the two starting wheat bran materials agrees fairly well with the reported values from the literature, as it can be observed in Table 1. The most abundant fatty acids in the two bran materials are oleic acid, palmitic acid, stearic acid and linoleic acid, in agreement with similar profiles.[1,6,7] Ferulic acid accounts for the principal phenolic acid in wheat bran, with lower content of p-coumaric acid; no traces of syringic acid were detected in this study. Our amino acid profile shows a high prevalence of valine and aspartic acid; this profile is different from previous studies, which report higher amounts of glutamic acid, aspartic acid, arginine, proline, leucine, serine, and phenylalanine.11,12

TABLE 3

General composition of raw wheat bran (fine and medium granulometry) and (defatting and destarching) material after initial pre-treatments

| | Raw wheat bran | | Defatted and destarched wheat | |
|---|---|---|---|---|
| General composition | Fine bran (wbf) | Medium bran (wbf) | Fine bran (Dwbf) | Medium bran (Dwbf) |
| Moisture (%)[a] | 23.3 (0.5) | 24.2 (1.7) | 18.5 (1.1) | 10.4 (0.9) |
| Carbohydrate content (mg/g DW)[b] | 395.4 (17.8) | 550.0 (29.3) | 562.1 (37.2) | 533.1 (51.5) |
| Fuc (%) | 0.2 (0.1) | 0.1 (0.0) | 0.1 (0.0) | 0.1 (0.1) |
| Ara (%) | 30.6 (0.2) | 35.5 (0.4) | 33.6 (1.0) | 35.7 (1.2) |
| Gal (%) | 4.3 (0.2) | 3.2 (0.1) | 8.8 (0.9) | 8.6 (1.1) |
| Glc (%) | 31.3 (0.7) | 24.5 (0.1) | 22.3 (1.0) | 24.1 (0.6) |
| Xyl (%) | 32.6 (0.7) | 35.7 (0.1) | 33.9 (0.7) | 30.6 (1.8) |
| Man (%) | 0.6 (0.1) | 0.5 (0.0) | 0.7 (0.1) | 0.5 (0.2) |
| GalA (%) | 0.2 (0.1) | 0.2 (0.0) | 0.2 (0.0) | 0.1 (0.1) |
| GlcA (%) | 0.3 (0.2) | 0.4 (0.1) | 0.3 (0.1) | 0.2 (0.1) |
| Starch (mg/g DW)[c] | 172.5 (0.5) | 154.3 (0.3) | n.d. | n.d. |
| Protein content (mg/g DW)[d] | 141.3 (14.1) | 196.6 (61.1) | 140.1 (2.5) | 155.30 ± 4.68 |
| Val (%) | 34.2 (1.8) | 32.0 (0.5) | 30.1 (0.1) | 30.2 (0.1) |
| Ala (%) | 2.9 (0.3) | 1.9 (0.1) | 3.0 (0.1) | 2.2 (0.0) |
| Leu (%) | 1.7 (0.3) | 2.5 (0.0) | 1.4 (0.1) | 2.7 (0.0) |
| Ile (%) | 6.3 (0.2) | 93 (0.1) | 6.3 (0.0) | 8.3 (0.1) |
| Asp (%) | 36.6 (0.8) | 32.9 (0.6) | 32.4 (0.6) | 33.5 (0.4) |
| Glu (%) | 5.8 (0.1) | 7.8 (0.2) | 9.0 (0.1) | 8.0 (0.1) |
| Phe (%) | 19 (0.1) | 2.3 (0.0) | 5.2 (0.0) | 1.9 (0.0) |
| Trp (%) | 10.6 (0.0) | 12.2 (0.1) | 12.5 (0.0) | 13.2 (0.0) |
| Phenolic acid content (mg/g DW)[e] | 2.2 (0.1) | 2.1 (0.1) | 2.4 (0.3) | 2.5 (0.3) |
| | 3.2 (0.4) | 11 (0.2) | 9.7 (1.2) | 10.1 (1.1) |
| ferulic acid (%) | 96.8 (0.6) | 98.9 (0.6) | 90.3 (1.2) | 89.9 (1.1) |
| Fat content (mg/g DW)[f] | 44.5 (2.0) | 46.1 (0.6) | n.a. | n.a. |
| C12:0 (%) | 0.5 (0.1) | 0.4 (0.1) | | |
| C14:0 (%) | 5.4 (0.3) | 6.0 (0.5) | | |
| C15:0 (%) | 1.3 (0.1) | 1.1 (0.1) | | |
| C16:0 (%) | 16.3 (0.3) | 19.2 (2.4) | | |
| C18:0 (%) | 9.9 (0.3) | 11.4 (0.2) | | |
| C181 (%) | 52.9 (1.2) | 44.5 (1.3) | | |
| C18.2 (%) | 10.0 (0.4) | 12.8 (0.7) | | |
| C20:0 (%) | 3.4 (0.1) | 3.5 (0.9) | | |
| C22:0 (%) | 0.3 (0.2) | 0.3 (0.2) | | |
| C26:0 (%) | 1.0 (0.2) | 0.8 (0.2) | | |
| Klason lignin (mg/g)[g] | 9.0 (3.8) | 9.4 (1.3) | 11.7 (1.4) | 14.0 (1.0) |

[a]Moisture content was determined gravimetrically after drying in a oven at 110° C. for 24 hr.
[b]Carbohydrate content was determined by acid hydrolysis (H2SO4) and HPAEC-PAD analysis. Monosaccharides: Fuc-fucose, Ara-arabinose, Rha-rhamnose, Gal-galactose, Glc-glucose, Xyl-xylose, Man-mannose, GalA-galacturonic acid, GlcA-glucuronic acid.
[c]Starch content was determined gravimetrically after enzymatic treatment with α-amylase
[d]Protein content was determined by hydrolysis, derivatization and GC-MS analysis. Amino acids: Val-valine, Ala-alanine, Leu-leucine, Ile-isoleucine, Asp-aspartic acid, Glu-glutamic acid, Phe-phenylalanine, Trp-tryptophan.
[e]Phenolic acid content was determined by saponification, derivatization and GC-MS analysis.
[f]Total fat content was determined by weight difference after defatting using CH3Cl: MeOH (3:1, v/v). Fatty acids: C12:0-lauric acid; C14:0-myristic acid, C15:0-pentadecylic acid, C16:0-palmitic acid; C18:0-stearic acid; C18:1-oleic acid, C18:2-linoleic acid; C20:0-arachidic acid; C22:0-behenic acid; C26:0-cerotic acid.
[g]Klason lignin was determined gravimetrically from the residue after acid hydrolysis (H2SO4)

The carbohydrate content and composition differs significantly between fine and medium wheat bran, the latter having a higher overall AX content. The extraction procedures were optimized only for the fine material (wbf), since higher yields are expected due to enhanced mass transfer at lower particle sizes. The defatting and destarching pre-treatments are expected to remove the fatty acid and starch components from wheat bran, respectively. The Glc content decreased for the fine wheat bran sample after destarching (Dwbf), confirming the efficiency of the enzymatic hydrolysis. Surprisingly, the Glc content remains very similar for the medium wheat bran sample; this could indicate that the material was effectively destarched prior to delivery. It is worth mentioning that the enzymatic process by α-amylase may cause the removal of some water-soluble compounds, which may cause an overestimation of the starch content measured gravimetrically.

4.2 Alkaline Extractions

Alkaline extraction is the standard procedure for the extraction of hemicelluloses from biomass feedstock with low to medium yields. Extraction in NaOH has been widely used for the extraction of arabinoxylans from wheat bran.[1,13] Bivalent hydroxides such as Ca(OH)2 and Ba(OH)2 have been proposed as selective extractants for arabinoxylans.[14,15] However, it is well known that high pH conditions during extraction causes the modification of the native structure of the arabinoxylans. Here NaOH and Ca(OH)2 extraction have been selected as benchmark extraction methods for comparison purposes. Table 2 compares the yields and the composition after alkaline extraction of destarched wheat bran. The obtained extraction yields with NaOH are in the same range albeit slightly higher than those reported in similar studies (18-22%), evidencing the effectiveness of the extraction conditions[1,13]. The NEwb extract has high arabinoxylan content, although the presence of glucose (assignable to mixed-linkage 3-glucan) is noticeable. The more selective Cmixed-linkage 3-glucan) is noticeable. The more selective Ca(OH)2 extraction offered significant lower yields compared with NaOH but with higher AX purity. However, in both cases further purification of the extracts is required to achieve pure AX fractions. The phenolic acid content of the extract and residue fractions is largely reduced after alkaline extraction, which indicates that these valuable functionalities have been cleaved and released by the high pH values during extraction.

4.3 Hydrothermal Extraction

Hydrothermal extraction was carried out using pressurized hot water under different temperature (120° C., 140° C., and 160° C.) and pH conditions to compare the effects on the yield and composition of the extracts and residues.

A preliminary study of the evolution of the extraction was undertaken by performing three successive steps of 5 minutes at each condition (FIG. 3). The glucan composition in the extracts is higher for short times in all the conditions, whereas the AX composition increases progressively with extraction time. These results indicate the different extractability of the hemicellulosic components in wheat bran; glucans seem to be more accessible and easier solubilized that AX. Moreover, the AX ratio also decreases consistently during extraction times; the AX populations with A/X ratio around 0.8-0.9 are easier extractable than that with lower Ara content (A/X 0.6). This may offer indirect information about the intermolecular associations of the polymeric components in wheat bran.

The three extraction steps at each condition were combined into one sample and further composition analyses were performed (Table 3). Higher extraction temperatures increase the yields from hydrothermal extraction, although the yields are somewhat lower than those obtained from NaOH extraction. The extracts have high AX content with marked presence of glucans, with increasing AX content with temperature. The residues have still high AX content, which correspond with unsolubilized fractions that may be highly cross-linked. The phenolic acids seem to be preserved after hydrothermal extraction. It is worth mentioning the high ferulic acid content in the residues, which suggests the presence of feruloylated AX fractions that has not been solubilized by hydrothermal extraction.

TABLE 4

Yields and composition of the fractions obtained from alkaline extraction

|  | NaOH extraction | | Ca(OH)2 extraction | |
| --- | --- | --- | --- | --- |
|  | NEwb | NRwb | CEwb | CRwb |
| Yield (% DW)[a] | 31.3 | 14.8 | 12.4 | 37.0 |
| Carbohydrate content (mg/g)[b] | 834.2 (23.5) | 793.2 (46.3) | 740.0 (57.2) | 704.9 (64.9) |
| AX (%)[c] | 82.9 (0.2) | 26.2 (1.7) | 89.0 (0.9) | 44.3 (3.5) |
| Glc (%)[d] | 12.6 (0.1) | 67.7 (1.6) | 5.6 (0.5) | 47.4 (1.4) |
| A/X[e] | 0.90 | 0.79 | 1.09 | 0.65 |
| Protein content (mg/g)[f] | 125.9 (7.7) | — | 149.8 (13.8) | 100.0 (10.0) |
| Phenolic acid content (mg/g)[g] | 1.3 (0.4) | 1.1 (0.1) | 0.8 (0.0) | 0.8 (0.1) |
| Ferulic acid (%)[h] | 78.7 (0.6) | 94.5 (1.8) | 90.4 (1.8) | 100 (0.0) |

NOTES:
Standard deviation is presented ().
[a]Yields for the extracts and residues were calculated gravimetrically as % dry weight of Dwbf
[b]Carbohydrate content was determined after acid hydrolysis (TFA hydrolysis for the extracts, H2SO4 hydrolysis for the residues) and HPAEC-PAD analysis.
[c]Arabinoxylan (AX) content was calculated based on the total Ara and Xyl composition. This value includes the residual Ara potentially present in arabinogalactan (pectin).
[d]Glc content can be potentially assigned to mixed-linkage 3-glucans in the extracts after TFA hydrolysis and to cellulose in the residues after $H_2SO_4$ hydrolysis.
[e]A/X is the ratio between arabinose (Ara) and xylose (Xyl)
[f]Protein content was determined by amino acid quantification after hydrolysis and GC-MS analysis.
[g]Phenolic acid content was determined by total phenolic acid quantification after saponification, derivatization and GC-MS analysis.
[h]The ferulic acid content is presented as % of the total phenolic acid content.

TABLE 5

Yields and composition of the fractions obtained from hydrothermal extraction.

| | Pressurized hydrothermal extraction | | | | | | | | | |
|---|---|---|---|---|---|---|---|---|---|---|
| | 120° C. | | 140° C. | | 160° C. | | | | | |
| | pH 5 | | pH 5 | | pH 5 | | pH 7 | | pH 9 | |
| | HE | HR | HE | HR | HE | HR | HE | HR | HE | HR |
| Yield (% DW)[a] | 9.2 | 42.5 | 15.6 | 26.6 | 20.9 | 39.0 | 22.3 | 39.3 | 15.1 | 38.0 |
| Carbohydrate content (mg/g)[b] | 882.0 (57.9) | 730.1 (45.6) | 905.2 (58.2) | 692.8 (26.3) | 858.6 (43.8) | 622.0 (67.9) | 827.4 (27.6) | 712.7 (71.7) | 744.9 (67.3) | 763.1 (76.5) |
| AX (%)[c] | 66.6 (0.5) | 44.4 (2.0) | 69.8 (1.5) | 60.9 (0.4) | 75.6 (0.9) | 57.5 (0.1) | 76.5 (2.9) | 60.1 (0.6) | 74.8 (0.9) | 59.1 (1.0) |
| Glc (%)[d] | 27.0 (0.5) | 50.0 (1.2) | 24.1 (1.2) | 31.9 (0.4) | 19.0 (0.8) | 36.4 (0.3) | 18.5 (2.2) | 34.4 (0.3) | 19.9 (0.8) | 35.9 (0.7) |
| A/X[e] | 0.67 | 1.15 | 0.63 | 1.27 | 0.57 | 1.39 | 0.59 | 1.08 | 0.65 | 1.04 |
| Protein content (mg/g)[f] | 150.0 (3.4) | 23.9 (0.0) | 74.6 (0.2) | 103.1 (6.5) | 132.8 (2.9) | 75.9 (1.0) | 103.9 (0.6) | 130.6 (4.4) | 41.5 (1.6) | 158.2 (0.8) |
| Phenolic acid content (mg/g)[g] | 2.2 (0.4) | 3.8 (0.4) | 4.3 (0.1) | 8.1 (0.3) | 1.5 (0.3) | 8.7 (0.4) | 1.7 (0.4) | 6.8 (0.3) | 1.5 (0.1) | 3.5 (0.2) |
| Ferulic acid (%)[h] | 92.6 (1.0) | 94.1 (0.5) | 93.6 (1.7) | 97.1 (0.7) | 87.9 (1.6) | 97.6 (0.3) | 76.3 (3.2) | 98.2 (0.1) | 89.9 (0.8) | 97.7 (0.3) |

NOTES: Standard deviation is presented ().
[a]Yields for the extracts and residues were calculated gravimetrically as % dry weight of Dwbf.
[b]Carbohydrate content was determined after acid hydrolysis (TFA hydrolysis for the extracts, H2SO4 hydrolysis for the residues) and HPAEC-PAD analysis.
[c]Arabinoxylan (AX) content was calculated based on the total Ara and Xyl composition. This value includes the residual Ara potentially present in arabinogalactan (pectin).
[d]Glucose content can be potentially assigned to mixed-linkage β-glucans in the extracts after TFA hydrolysis and to cellulose in the residues after $H_2SO_4$ hydrolysis.
[e]A/X is the ratio between arabinose (Ara) and xylose (Xyl)
[f]Protein content was determined after hydrolysis, derivatization and GC-MS analysis.
[g]Phenolic acid content was determined after saponification, derivatization and GC-MS analysis.
[h]The ferulic acid content is presented as % of the total phenolic acid content.

4.4 Molar Mass Distributions of the Extracts from Wheat Bran

FIG. 4 shows the molar mass distributions of the wheat bran extracts using different conditions. In general a high molar mass fraction can be observed for all the extracts ($10^5$-$10^6$ g/mol), with significant presence of low molar mass impurities (103-104 g/mol) that could be attributed to proteins and oligosaccharides. The average molar masses ($M_w$) and the dispersity index (D) are also reported. Alkaline extraction offers AX fractions with larger molar mass, of around $4 \times 10^5$ g/mol. The AX fractions extracted from hydrothermal treatment have slighter lower molar mass than their alkaline counterparts, which can be attributed either to degradation during the high temperature during extraction, or to the fact that larger AX populations cannot be solubilized under those conditions. Higher temperatures and lower pH values seem to slightly reduce the molar mass of the fractions.

5. Discussion

Two wheat bran materials with different granulometry are evaluated to exhibit different carbohydrate content and composition. The AX content in the medium grain wheat bran is slightly higher.

Alkaline extraction with NaOH offers the highest material yields but it reduces significantly the amount of phenolic functionalities. Hydrothermal extraction has been evaluated at different temperature and pH conditions. In one embodiment, 160° C. and pH7 is found to be optimal conditions for hydrothermal extraction in terms of yield, AX content, and molar mass of the extracts. All extraction procedures exhibit appreciable amounts of low molar mass compounds (probably protein and oligomeric fractions) and glucans (probably mixed-linkage β-glucan). Further purification steps by membrane filtration and enzymatic treatments can be employed to obtain AX fractions with high purity. Feruloylated AX fractions present in the residues after hydrothermal extraction can be isolated using enzymatic approaches. Feruloylated AXs constitute an extremely valuable fraction with very interesting functionalities that could be used as antioxidant or UV absorbant additives in AX-based materials.

Experiment 2

Objective

The objective of this experiment was to design an integrated bioprocess combining pressurized hot water extraction (PHWE), enzymatic treatments, and membrane ultrafiltration to fractionate high molar mass hemicelluloses rich in arabinoxylan with covalently bound ferulic acid (feruloylated arabinoxylan) from low molar mass oligosaccharides. By preserving the feruloylated content of these polymeric and oligomeric fractions, additional antioxidant properties and potentially UV-absorbant value were conferred to these fractions. These novel functionalities provide interesting multifunctional properties as antioxidant and UV-absorbant to the prepared AX-based films and gels, in addition to their barrier and rheological properties.

3.1 Materials

Wheat bran with fine granulometry ($wb_f$) was provided by Lantmännen. All chemicals, analytical standards and reagents were from Sigma-Aldrich. α-Amylase porcine pancreatic was purchased from Sigma-Aldrich. Pholin Ciocalteau Phenol reagent was from Merck. Spectra/Por 1 and 3 Dialysis Membrane, 6-8 kD and 3.5 kDa MWCO, and Biotech CE dialysis tubing, 0.1-0.5 kDa and 20 kDa MWCO were purchased from SpectrumLabs. Centramate cassete 30kMWCO was purchased from VWR. Feruloyl esterase 1A (*Ruminococcus albus*) was purchased from NZytech. Endo-1,4-β-xylanase (GH10) was purchased from Megazyme.

3.2 Bioprocess Design

The combined extraction procedures and the different materials and fractions obtained are summarized in FIG. 7. The extended description of the extraction procedures is provided in experiment 1. Here, focus is on the new developed tasks.

3.2.1 Defatting and Destarching

The wheat bran ($wb_f$) was defatted by chloroform ($CHCl_3$) and methanol (MeOH). The total fat content was determined according to Folch method.[1] The defatted bran was enzymatically destarched with α-amylase. Total starch content was determined using the total starch kit (Megazyme, Ireland) before and after the α-amylase treatment.

3.2.2 Alkaline and Hydrothermal Pressurized Hot Water (PHWE) Extraction

Defatted and destarched wheat bran ($Dwb_f$) was extracted with 0.5M NaOH or $Ca(OH)_2$ at 80° C. for 16 h using a ratio of 1:8 (w/v). Pressurized hot-water extraction (PHWE) of $Dwb_f$ was performed at different temperatures (100, 120, 140 and 160° C.) and pH (5.0, 7.0, and 9.0) using 1M sodium formate/formic acid buffer. The extractions were done in three subsequent cycles of 5 min, resulting in 3 extracts and 1 residue for each tested condition.

3.2.3 Membrane Filtration

The different extracts after PHWE were solubilized in water at 10 mg $mL^{-1}$ and submitted to closed dialysis using a 20 kDa MWCO membrane for 48 h. The collected eluents and retentates were concentrated in a rotavapor and freeze-dried. Membrane ultrafiltration was upscaled for the HE-160-7 extracts in a continuous flow (initial concentration 10 mg $mL^{-1}$), using a 30 kDa cassette membrane ultrafiltration device. The retentate (high molar mass) and the eluent (low molar mass), were collected separately, concentrated and freeze-dried.

3.2.4 Enzymatic Treatments

The residue of PHW extraction was treated enzymatically to further valorize the crosslinked insoluble residue after pressurized hot water extraction. The residues were incubated with feruloyl esterase 1A alone or in synergy with an endo-1,4-β-xylanase in water (20 mL) at 37° C. for 16 h. The incubations were centrifuged, and both supernatant and residue were freeze-dried. The supernatants generated after the enzymatic incubations were used for the quantification of the reducing sugars (DNS assay) and for oligosaccharide analysis by ESI-MS. The residues after enzymatic treatment were further submitted to a new PHW extraction at 160° C. pH 7.0 (3.2.2).

3.3 Characterization of the Extracted Fractions

3.3.1 Monosaccharide Content and Composition

The monosaccharide content and composition of the wheat bran and the fractions was analyzed by acid hydrolysis followed by high-pH anion exchange chromatography with pulsed amperometric detection (HPAEC-PAD) (see Experiment 1 for full details).[2,3]

3.3.2 Phenolic Content and Composition

The phenolic acid content and composition was determined by saponification, silylation and GC-MS[4] (see Experiment 1 for the full analytical description).

3.3.3 Glycosidic Linkage Analysis

Glycosidic linkage analysis was performed by methylation under alkaline conditions (excess of NaOH) in dimethyl sulfoxide (DMSO) using the conditions reported by Ciucanu & Kerek. The partially methylated polysaccharides were hydrolyzed with 2 M TFA at 121° C. for 3 h and further derivatized into permethylated alditol acetates (PMAAs) by reduction with $NaBH_4$ and acetylation with acetic anhydride and pyridine. The PMAAs were identified and quantified by GC-MS on a SP-2380 capillary column (30 m×0.25 mm ID, Agilent Technologies) with a temperature ramp of 1° C. $min^{-1}$ from 160 to 210° C.

3.3.4 Molar Mass Distributions by SEC

The molar mass distributions of the extracted arabinoxylans from wheat bran were analysed by size exclusion chromatography coupled to refractive index and multi-angle laser light scattering (see Experiment 1 for the full analytical description).

3.3.5 Dinitrosalicylic Acid (DNS) Method—Reducing Sugar Determination 1 mL of the standard (glucose; 10 µmol $L^{-1}$) or sample was mixed with 1 mL of DNS reagent, vortexed and incubated in a boiling water bath for 15 min. After cooling in an ice bath, the volume was completed to 10 ml and the absorbance measured in spectrophotometer at 540 nm against a reagent blank. Calibration was performed using glucose standard solutions.

3.3.6 Oligosaccharide Fingerprinting by ESI-MS

Electrospray ionization mass spectrometry (ESI-MS) was performed to identify the oligosaccharides from enzymatic incubations. The samples were filtered (3 kDa Amicon, 11500 rpm, 15 minutes) and directly injected into the ESI-MS (Q-Tof-2, Waters) in positive mode with cone voltage 80 V, capillary voltage 3.3 kV, and desolvation temperature 140° C.

3.3.7 Antioxidant Activity

The antioxidant activity of the alkaline and PHWE extracts was evaluated according to the reduction of the DPPH radical in methanolic solution with the presence of an antioxidant donor.[5] Briefly, 1.5 mL sample aliquots at different concentrations (10-100 µg $mL^{-1}$) were mixed with 0.5 mL of 100 µM $L^{-1}$ methanolic solution of DPPH. Wheat endosperm arabinoxylan (WE-AX) was used as a negative control, while ascorbic and ferulic acid were used as positive controls. The reaction mixture was incubated for 30 min in the dark at room temperature and the absorbance was measured in a spectrophotometer at 515 nm. The radical scavenging activity was measured as the absorbance decrease of DPPH (equation 1):

$$\text{Scavenging activity} = (1 - A_{sample}/A_{control}) \times 100 \quad (1)$$

where $A_{sample}$ was the absorbance in the presence of the sample, and $A_{control}$ was the absorbance of the control containing the reaction reagents except the sample or the positives or negative controls. All determinations were performed in triplicate.

4. Results

Table 6 presents a summarised version of the composition of the wheat bran with fine granulometry ($wb_f$) and after defatting and destarching ($Dwb_f$). The general composition of the starting wheat bran agrees well with the reported values from the literature, with AX being the main polysaccharide component (approximately 24-36% in DW), proteins accounting for approximately 15% and a small amount of ferulic acid (0.2% DW), with significant importance in the crosslinking of the bran structure. Defatting and destarching treatment successfully remove the fatty acid and starch components.

TABLE 6

General composition of fine wheat bran ($wb_f$) and after defatting and destarching ($Dwb_f$)

| General Composition | $wb_f$ | $Dwb_f$ |
|---|---|---|
| Moisture (%)[a] | 22.0 | 18.4 |
| Total Carbohydrate (mg $g^{-1}$ DW)[b] | 595.9 (0.6) | 682.4 (0.09) |
| AX (%) | 48.6 (0.9) | 59.4 (0.4) |
| A/X | 0.59 | 0.66 |
| Glc (%) | 45.5 (0.7) | 35.7 (0.9) |
| Starch (mg $g^{-1}$ DW)[c] | 169.4 (0.6) | 28.9 (2.9) |
| β-glucan (mg $g^{-1}$ DW)[d] | 57.0 (3.0) | 60.8 (1.0) |
| Protein (mg $g^{-1}$ DW)[e] | 202 | 197 |
| Fats (mg $g^{-1}$ DW)[f] | 44.5 (2.0) | — |
| Phenolics (mg $g^{-1}$ DW)[g] | 2.2 (0.1) | 2.4 (0.3) |
| Ferulic acid (mg $g^{-1}$ DW) | 1.9 (0.1) | 2.3 (0.1) |
| Lignin (mg $g^{-1}$ DW)[h] | 90.0 (3.8) | 1178 (14) |

[a]Moisture content was determined gravimetrically after drying in a oven at 110° C. for 24 h;
[b]Carbohydrate content was determined by phenol-sulphuric acid method;
[c]Starch content was determined enzymatically using the total starch kit (Megazyme);
[d]β-glucan content was determined enzymatically using the mixed-linkage β-glucan kit (Megazyme);;
[e]Protein content was determined using Dumas method (Lantmännen-Cereal Laboratoriet);
[f]Total fat content was determined by weight difference after defatting using $CH_3Cl$: MeOH (3:1, v/v);
[g]Phenolic acid content was determined by saponification, derivatization and GC-MS analysis;
[h]Klason lignin was determined gravimetrically from the residue after acid hydrolysis ($H_2SO_4$).

4.1 Comparison of Pressurised Hot Water Extraction and Alkaline Extraction

Alkaline extraction is the standard procedure for the extraction of hemicelluloses from biomass feedstock. However, high pH conditions during extraction causes the modification of the native structure and the cleavage of the valuable phenolic substitutents (e.g. ferulic acid). In this project we propose pressurized hot-water extraction as an alternative method to release the polymeric AX fractions while maintaining the ferulic acid functionalities.

In experiment 1 we presented the yields and composition of the extracts and the residues after alkaline and PHW extraction using different temperature and pH conditions. These have been extended (100° C. pH 5) and summarised in FIG. 9. Alkaline extraction with NaOH offers the highest yield (30% in DW). Temperature and pH conditions for PHWE have been optimised at 160° C. pH 7 and offer lower but comparable yields than alkaline extraction with NaOH. However, with PHWE we achieve similar AX content and we maintain the ferulic acid functionalities both in the extract and in the residue. Interestingly, the residue after PHWE still contains over 50% of unextractable AX with high FerA content assigned to crosslinked material (FIG. 8), which constitutes still a valuable resource of F-AX for further recovery.

4.2 Membrane Separation of the Extracts

The alkaline and PHW extracts were subjected to membrane ultrafiltration to isolate the low molar mass permeates from the high molar mass retentates. The procedure was capable of clearly separating the oligosaccharides (HE-160-7-L) from the polymeric fractions with molar masses in the range of $10^5$-$10^6$ g $mol^{-1}$ (HE-160-7-H) (FIG. 9).

Table 7 presents the number-average molar mass (Mn) and the weight-average molar mass from the permeates (L) and retentates (H) after membrane ultrafiltration. The permeates correspond with oligosaccharide populations with molar masses between 1000-2000 g $mol^{-1}$. The retentates, on the contrary, correspond with polysaccharide populations with molar masses in the range of $10^5$-$10^6$ g $mol^{-1}$. Polysaccharides from the alkaline extracts, NaOH (NE) and Ca(OH)$_2$ (CE) exhibit higher molar mass than the ones extracted by hydrothermal PHW extraction. This could be attributed to the disruption of the ferulic crosslinks between hemicellulosic fractions, which enhances the extraction of larger polymeric populations, in agreement with the results from FIG. 8.

TABLE 7

Average molar masses of the polymeric (H) and oligomeric fractions (L) of the wheat bran extracts after membrane ultrafiltration

| Extracts | High molar mass retentate (H) | | Low molar mass permeate (L) | |
|---|---|---|---|---|
| | Mw | Mn | Mw | Mn |
| NE | 458340 | 135640 | n-a. | n.a |
| CE | 468790 | 209850 | n.a. | n.a |
| HE-120 | 182170 | 69622 | 1494 | 1060 |
| HE-140 | 138410 | 67330 | 1048 | 833 |
| HE-160-5 | 133920 | 82419 | 1763 | 1314 |
| HE-160-7 | 193980 | 135040 | 1048 | 839 |
| HE-160-9 | 187840 | 106100 | 1920 | 1551 |

4.2.1 Molecular Structure of the Polysaccharide Fractions after Membrane Filtration The molecular structure of the high molar mass polysaccharide fractions extracted under different alkaline and PHWE conditions was characterised by glycosidic linkage analysis (Table 8). This offers information about the content of the different polysaccharide populations present in the extracts and about the substitution pattern of the F-AX populations in terms of unsubstituted (→4)-Xylp-(1→), monosubstituted (→2,4)-Xylp-(1→ and →3,4)-Xylp-(1→) and disubstituted (→2,3,4)-Xylp-(1→) backbone units. From the assignation of the glycosidic linkages, we can identify the presence of pectin populations (mainly arabinogalactans 3-5%), mixed-linkage β-glucans (15-20%) and arabinoxylans (70-80%). Interestingly, the polysaccharide molecular structure influences the extractability under PHWE extraction. Pectins and mixed-linkage 3-glucans seem to be easier extracted, whereas the AX content increases progressively with higher temperatures and extraction times. In addition to this, higher extraction temperatures and times result in F-AX populations with higher ratio of substituted Xylp units and higher ferulic acid content. This indicates that we can control the structure and composition of the polysaccharide fractions by choosing the extraction conditions, which will become useful during the preparation of the carbohydrate-based materials.

TABLE 8

Monosaccharide composition and glycosidic linkage analysis of the high molar mass polysaccharide fraction (H) after membrane ultrafiltration

| | NE-H | HE-120-H | HE-140-H | HE-160-5-H | HE-160-7-H 5' | HE-160-7-H 10' | HE-160-7-H 15' | HE-160-9-H |
|---|---|---|---|---|---|---|---|---|
| Yields (% DW)[a] | 79.1 | 68.8 | 78.3 | 58.6 | 26.9 | 22.3 | 16.7 | 76.8 |
| Carbohydrate content (mg g$^{-1}$ DW)[b] | 871.9 (3.4) | 839.9 (24.9) | 715.8 (7.6) | 815.4 (1.8) | 618.7 (5.2) | 536.3 (3.4) | 778.6 (7.3) | 863.1 (0.4) |
| Total Ara (%)[c] | 40.7 | 29.5 | 25.6 | 24.6 | 28.5 | 25.9 | 19.5 | 22.7 |
| Araf-(1→ | 31.0 | 23.5 | 20.3 | 18.9 | 23.6 | 19.3 | 14.7 | 18.6 |
| →2)-Araf-(1→ | 2.1 | 1.5 | 1.5 | 1.4 | 1.6 | 21 | 1.1 | 1.4 |
| →3)-Araf-(1→ | 5.0 | 1.4 | 1.5 | 1.2 | 1.8 | 1.8 | 2.2 | 1.6 |
| →5)-Araf-(1→ | 1.7 | 2.4 | 1.8 | 2.7 | 1.3 | 1.7 | 1.4 | 1.1 |
| →2,3,5)-Araf(1→ | n.d. | 0.8 | 0.7 | 0.5 | 0.2 | 1.1 | 0.2 | n.d. |
| Total Xyl (%)[c] | 55.3 | 47.8 | 49.0 | 49.1 | 45.4 | 56.6 | 65.4 | 41.4 |
| Xylp-(1→ | 5.51 | 2.4 | 0.3 | 1.8 | 2.3 | 2.2 | 3.2 | 2.5 |
| →4)-Xylp-(1→ | 26.40 | 28.2 | 31.2 | 30.0 | 36.7 | 29.8 | 24.9 | 39.4 |
| →2,4)-Xylp-(1→ | 3.75 | 2.6 | 3.1 | 3.2 | 3.0 | 5.1 | 6.6 | 4.1 |
| →3,4)-Xylp-(1→ | 7.83 | 5.5 | 5.0 | 6.5 | 5.1 | 8.2 | 10.1 | 7.7 |
| →2,3,4)-Xylp-(1→ | 11.78 | 9.1 | 8.7 | 7.5 | 9.5 | 7.8 | 7.3 | 9.0 |
| Total Glc (%)[c] | 2.3 | 15.6 | 22.0 | 20.9 | 21.7 | 14.0 | 13.0 | 12.3 |
| Glcp-(1→ | 0.2 | 1.3 | 3.0 | 2.4 | 2.2 | 1.0 | 1.1 | 1.2 |
| →3)-Glcp-(1→ | 0.3 | 2.3 | 7.0 | 5.8 | 5.3 | 4.9 | 4.5 | 3.1 |
| →4)-Glcp-(1→ | 1.3 | 10.1 | 11.6 | 12.8 | 13.4 | 8.9 | 7.8 | 7.7 |
| Total Gal (%)[c] | 3.8 | 6.3 | 3.2 | 5.1 | 3.8 | 2.2 | 1.9 | 2.2 |
| Galp-(1→ | 1.3 | 1.7 | 0.8 | 0.9 | n.d | n.d. | n.d. | 0.8 |
| →3)-Galp-(1→ | 0.5 | 0.8 | 0.7 | 0.8 | n.d | n.d. | n.d. | 0.3 |
| →4)-Galp-(1→ | 1.1 | 0.3 | 0.7 | 1.3 | 0.3 | 0.8 | 0.6 | 0.6 |
| →3,6)-Galp-(1→ | 1.9 | 3.6 | 1.0 | 1.8 | 1.0 | 0.5 | 0.3 | 0.3 |
| Protein content (mg g$^{-1}$ Dw)[d] | 104.1 (2.2) | 109.7 (32.5) | 88.9 (6.2) | 78.0 (5.3) | 81.0 (1.9) | 79.8 (3.3) | 117.2 (4.3) | 71.2 (1.5) |
| Ferulic acid content (mg g$^{-1}$ DW)[e] | 0.2 (0.04) | 4.6 (0.14) | 4.5 (0.13) | 4.4 (0.14) | 2.4 (0.7) | 5.0 (0.06) | 7.5 (0.15) | 1.0 (0.1) |

[a] The yields were based on the dry weight of the extracts
[b] Carbohydrate content was determined by phenol-sulphuric acid method;
[c] The monosaccharide composition and linkages were determined by methylation analysis
[d] Protein content was determined by Bradford analysis
[e] Ferulic acid content was determined by saponification, derivatization and GC-MS analysis;

4.2.2 Molecular Structure of the Oligosaccharide Fraction after Membrane Filtration The molecular structure of the oligosaccharide fractions after membrane filtration was as well studied by glycosidic linkage analysis (Table 9). The presence mainly of mixed-linkage can be observed. Mainly mixed-linkage β-glucan oligosaccharides (MLBGOs) and arabino-xylo-oligosaccharides (AXOs) are observed as the main components in the fractions. These oligosaccharides become useful as prebiotics in food formulations or as precursors for bio-based additives (e.g. plasticizers) in material applications.

TABLE 9

Monosaccharide composition and glycosidic linkage analysis of the low molar mass oligosaccharide fraction after membrane ultrafiltration

| | NE-L | HE-120-L | HE-140-L | HE-160-5-L | HE-160-7-L | HE-160-9-L |
|---|---|---|---|---|---|---|
| Yields (%) | 9.2 | 28.8 | 19.0 | 40.6 | 32.6 | 21.8 |
| Carbohydrate content (mg g$^{-1}$ DW) | 750.0 (4.5) | 616.3 (1.2) | 743.3 (9.9) | 564.2 (27.5) | 598.1 (7.1) | 660.6 (26.4) |
| Total Ara | 29.3 | 17.8 | 26.2 | 21.5 | 31.1 | 26.0 |
| Araf-(1→ | 19.6 | 8.4 | 16.6 | 16.1 | 19.2 | 19.8 |
| →2)-Araf-(1→ | 1.8 | n.d. | 1.4 | 1.3 | 0.9 | 1.7 |
| →3)-Araf-(1→ | 2.8 | 0.6 | 1.5 | 1.3 | 0.9 | 2.3 |
| →5)-Araf-(1→ | 1.8 | 6.2 | 2.8 | 2.7 | 6.2 | 1.6 |
| →2,3,5)-Araf-(1→ | n.d. | 2.1 | 2.6 | 0.2 | 3.8 | 0.6 |
| Total Xyl | 31.3 | 35.0 | 41.2 | 48.5 | 35.0 | 32.5 |
| Xylp-(1→ | 3.5 | 6.3 | 1.2 | 2.0 | 1.1 | 3.6 |
| →4)-Xylp-(1→ | 13.4 | 19.2 | 22.6 | 27.4 | 30.4 | 25.5 |
| →2,4)-Xylp-(1→ | 3.1 | 1.6 | 2.5 | 3.1 | 3.5 | 3.5 |

TABLE 9-continued

Monosaccharide composition and glycosidic linkage analysis of the low molar mass oligosaccharide fraction after membrane ultrafiltration

|  | NE-L | HE-120-L | HE-140-L | HE-160-5-L | HE-160-7-L | HE-160-9-L |
|---|---|---|---|---|---|---|
| →3,4)-Xylp-(1→ | 6.0 | 2.7 | 5.7 | 6.6 | 5.8 | 7.6 |
| →2,3,4)-Xylp-(1→ | 5.3 | 5.3 | 9.3 | 9.4 | 7.8 | 9.5 |
| Total Glc | 29.5 | 41.9 | 28.9 | 25.2 | 20.4 | 20.2 |
| Glcp-(1→ | 12.5 | 6.2 | 5.3 | 2.7 | 2.2 | 1.4 |
| →3)-Glcp-(1→ | 2.4 | 4.3 | 5.2 | 6.0 | 5.1 | 5.9 |
| →4)-Glcp-(1→ | 8.3 | 23.8 | 17.7 | 15.7 | 13.0 | 12.2 |
| →4,6)-Glcp-(1→ | 6.3 | 7.6 | 0.7 | 0.8 | n.d. | 0.7 |
| Protein content (mg g$^{-1}$ DW) | 51.6 (1.6) | 155.1 (24.9) | 71.1 (10.1) | 51.7 (2.4) | 46.3 (14.8) | 49.2 (3.4) |
| Ferulic acid content (mg g$^{-1}$ DW) | 0.2 (0.04) | 3.2 (0.14) | 1.0 (0.1) | 1.8 (0.13) | 3.2 (0.03) | 0.2 (0.1) |

4.3 Enzymatic Treatment of the Extraction Residue

The residues after PHWE still contained approximately 50% of AX (FIG. 8b), which constitutes a valuable resource for further recovery. The use of specific enzymes was tested to disrupt the crosslinked structure of the residue in order to further obtain valuable functional polysaccharides and oligosaccharides. In this direction, a feruloyl esterase (FE) was tested alone or in synergy with an endo-1,4-β-xylanase (X). The feruloyl esterase showed on its own residual action on the residue, but in combination with a β-xylanase/esterase showed on its own residual action on the residue as shown from the reducing sugar assay from the supernatant in FIG. 10a. The oligosaccharides consist of pentoses (arabino-xylo-oligosaccharides, AXOs) and feruloylated pentoses (F-AXOs) with 2-10 sugar units (FIG. 10b). This constitutes a proof of concept of the enzymatic action onto the crosslinked residue to release valuable functional oligosaccharides for nutritional and material purposes.

The residue after enzymatic action was subjected to another cycle of pressurized hot water extraction, which was capable of releasing further arabinoxylan. FIG. 11 compares the obtained yields after enzymatic treatment (EZ) and after combined enzymatic treatment with subsequent extraction (EZ+PHWE), together with the arabinoxylan content. This iterative procedure ensures the optimized recovery of arabinoxylan from the residue.

4.4 Antioxidant Activity of the AX Fractions from Wheat Bran

The antioxidant activity of the different fractions at different concentrations was evaluated by their scavenging activity in the DPPH radical test. The alkaline extract (NE-AX) shows very poor scavenging activity, similar to the water-extractable endosperm arabinoxylan (WE-AX) negative control, which can be assigned to the loss of ferulic acid functionalities during the aggressive alkaline conditions. Both the polysaccharide (HE-160-7-H) and oligosaccharide (HE-160-7-L) extracts after PHWE and membrane ultrafiltration show similar scavenging activity with respect to the positive controls (ascorbic and ferulic acid). These results show the potential of these fractions for the preparation of multifunctional barrier materials with additional radical scavenging activity in food contact applications (see FIG. 12).

The invention claimed is:

1. A process for producing and isolating feruloylated arabinoxylans (AXs), in polymeric form from a cereal crop, comprising
    a) subjecting said cereal crop to pressurized hot water extraction, whereby the extract and the water-unextractable residues from the hydrothermal extraction comprise feruloylated arabinoxylans;
    b) subsequent enzymatic treatment of the water-unextractable residues from step a) to isolate the water-unextractable feruloylated arabinoxylans from the water-unextractable residues; and
    c) purification treatment by means of membrane ultrafiltration and enzymatic hydrolysis.

2. A process according to claim 1, wherein the pressurized hot water extraction in step a) is performed at a temperature of between 140-160° C.

3. A process according to claim 1, wherein the pressurized hot water extraction in step a) is performed in a pH between pH 5-7.

4. A process according to claim 1, wherein the pressurized hot water extraction in step a) is performed at 160° C. in pH 5 or pH 7.

5. A process according to claim 1, wherein the pressurized hot water extraction in step a) is performed at a temperature of 160° C. and at pH 9.

6. A process according to claim 1, wherein the pressurized hot water extraction in step a) is performed at a temperature of 120° C. and at pH 5.

7. A process according to claim 1, wherein the enzymatic treatment comprises enzymes with polysaccharide activity.

8. A process according to claim 1, wherein different polysaccharide fractions are isolated from each other in step b) using chemo-enzymatic and chromatographic processes.

9. A process according to claim 1, wherein high molecular mass arabinoxylans are isolated.

10. A process according to claim 1, wherein the isolated arabinoxylans are selectively fractionated based on their molecular structure and inherent functionalities.

11. A process according to claim 1, wherein the cereal crop is selected from the group consisting of wheat bran, wheat grain, wheat flour, wheat straw, barley grain, Brewer's spent grain, barley flour, barley straw, rye grain, rye flour, rye bran, rye straw, oat grain, and oat bran.

12. A process for preparation of carbohydrate-based materials selected from the group consisting of films, hydrogels, active food packaging, prebiotics, bioactive compounds, and texturizing agents, comprising providing an isolated feruloylated arabinoxylan produced according to the process of claim 1.

13. A composition comprising both water-soluble and water-insoluble feruloylated arabinoxylans, wherein the ferulic acid content of the feruloylated arabinoxylans is at least 4 mg/g.

14. A carbohydrate-based material selected from the group consisting of films, hydrogels, active food packaging, prebiotics, and texturing agents, comprising an added feruloylated arabinoxylan composition according to claim 13.

* * * * *